US010435665B2

(12) United States Patent
Gerard et al.

(10) Patent No.: US 10,435,665 B2
(45) Date of Patent: Oct. 8, 2019

(54) METHOD OF CULTURING SEGMENTED FILAMENTOUS BACTERIA IN VITRO

(71) Applicants: INSTITUT PASTEUR, Paris (FR); FONDATION IMAGINE, Paris (FR); ASSISTANCE PUBLIQUE—HOPITAUX DE PARIS, Paris (FR); UNIVERSITE PARIS DESCARTES, Paris (FR); INSTITUT NATIONAL DE LA SANTE ET DE LA RECHERCHE MEDICALE (IN-SERM), Paris (FR)

(72) Inventors: Eberl Gerard, Paris (FR); Bikard David, Paris (FR); Schnupf Pamela, Paris (FR); Cerf Bensussan Nadine, Paris (FR); Gaboriau-Routhiau Valerie, Clamart (FR); Sansonetti Philippe, Paris (FR)

(73) Assignees: INSTITUT PASTEUR, Paris (FR); FONDATION IMAGINE, Paris (FR); ASSISTANCE PUBLIQUE—HOPITAUX DE PARIS, Paris (FR); INSTITUT NATIONAL DE LA SANTE ET DE LA RECHERCHE MEDICALE (INSERM), Paris (FR); UNIVERSITE PARIS DESCARTES, Paris (FR)

( * ) Notice: Subject to any disclaimer, the term of this patent is extended or adjusted under 35 U.S.C. 154(b) by 0 days.

(21) Appl. No.: 15/538,184

(22) PCT Filed: Dec. 23, 2015

(86) PCT No.: PCT/IB2015/059948
§ 371 (c)(1),
(2) Date: Jun. 20, 2017

(87) PCT Pub. No.: WO2016/103217
PCT Pub. Date: Jun. 30, 2016

(65) Prior Publication Data

US 2017/0335276 A1 Nov. 23, 2017

(30) Foreign Application Priority Data

Dec. 23, 2014 (WO) .................. PCT/IB2014/067285

(51) Int. Cl.
*C12N 1/20* (2006.01)
*C12N 15/74* (2006.01)
*C12N 13/00* (2006.01)

(52) U.S. Cl.
CPC ............... *C12N 1/20* (2013.01); *C12N 13/00* (2013.01); *C12N 15/74* (2013.01); *C12N 2502/23* (2013.01)

(58) Field of Classification Search
None
See application file for complete search history.

(56) References Cited

FOREIGN PATENT DOCUMENTS

WO WO 2011/046616 A2 4/2011

OTHER PUBLICATIONS

Marzorati et al., The HMI™ module: a new tool to study the Host-Microbiota Interaction in the human gastrointestinal tract in vitro, BMC Microbiology 2014, 14:133.*

Ulluwishewa et al., Live Faecalibacterium prausnitzii in an apical anaerobic model of the intestinal epithelial barrier, Cellular Microbiology (2015) 17(2), 226-240.*

Sczesnak et al., The Genome of Th17 Cell-Inducing Segmented Filamentous Bacteria Reveals Extensive Auxotrophy and Adaptations to the Intestinal Environment, Cell Host & Microbe 10, 260-272, Sep. 15, 2011.*

Schnupf et al., Host interactions with Segmented Filamentous Bacteria: An unusual trade-off that drives the post-natal maturation of the gut immune system, Seminars in Immunology 25 (2013) 342-351.*

Thermo Scientific publication, 5 reasons to enhance your cell culture using a Thermo Scientific CO2 incubator with variable oxygen control, published 2011. Downloaded by Office from: https://assets.thermofisher.com/TFS-Assets/LED/brochures/PFCO25TRIGASNA-CO2-Incubators.pdf.*

Senoh et al., Conversion of viable but nonculturable enteric bacteria to culturable by co-culture with eukaryotic cells, Microbiol Immunol 2012; 56: 342-345.*

E. J. Stewart: "Growing Unculturable Bacteria", Journal of Bacteriology, vol. 194, No. 16, Jun. 1, 2012 (Jun. 1, 2012), pp. 4151-4160.

S. J. Pamp et al: "Single-cell sequencing provides clues about the host interactions of segmented filamentous bacteria (SFB)", Genome Research, vol. 22, No. 6, Mar. 20, 2012 (Mar. 20, 2012), pp. 1107-1119.

Mitsutoshi Senoh et al: "Conversion of viable but nonculturable enteric bacteria? to culturable by co-culture with eukaryotic cells", Microbiology and Immunology, vol. 56, No. 5, Apr. 27, 2012 (Apr. 27, 2012), pp. 342-345.

European Patent Office, European Search Report in WO2016103217, dated Apr. 25, 2016.

* cited by examiner

*Primary Examiner* — Nancy J Leith
(74) *Attorney, Agent, or Firm* — Arrigo, Lee, Guttman & Mouta-Bellum LLP

(57) ABSTRACT

The present invention relates to an in vitro method of culturing a segmented filamentous bacterium strain, comprising co-culturing said segmented filamentous bacterium strain with a eukaryotic host cell, wherein the culture is performed at an $O_2$ level inferior to 5% in a rich tissue culture liquid medium containing bacterial medium components including iron. The present invention also relates to methods for genetically modifying a segmented filamentous bacterium strain comprising a step a culturing the strain in vitro.

45 Claims, 12 Drawing Sheets

Specification includes a Sequence Listing.

i

F

G

H

F

G

H e f

SEQUENCE LISTING

```
<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1

aggaggagtc tgcggcacat tagc                                              24


<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2

tccccactgc tgcctcccgt ag                                                22


<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

tcagtcgtca gcatggctcg c                                                 21


<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4

tccggtgggt ggcgtgagta tac                                               23


<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5

cagctgggct gtacaaacct t                                                 21
```

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
cattggaagt gaagcgtttc g 21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
catttgttca cgaggctttc c 21

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gtttttccag ttagcttcct tcatgt 26

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
tgtgtatccc acaaggtttc aga 23

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ttattaccct ctcctcctca agca 24

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
cgcagcacga gcaggat 17

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ccaggatcaa gatgcaaaga atg 23

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tggctgggat tcacctcaag 20

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
caagcctcgc gaccattct 19

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gccgtcattt tctgcctcat 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gcttccctat gcccctcatt 20

<210> SEQ ID NO 17
<211> LENGTH: 1758
<212> TYPE: DNA
<213> ORGANISM: Artificial Sequence
<220> FEATURE:
<223> OTHER INFORMATION: recombinant shuttle vector

<400> SEQUENCE: 17
gcggccgctc atttggtttt tcaaatggct tttttgtttt tttaaaagtt aatgcagtgt 60
aacactttta tagttttatc ataattttat aaaaaatata acgcataaat agagaaataa 120
ttatggatta ataaccaaaa ttatagtaaa atagttataa aatatattga ctttagtatg 180
cgaaatgtat taatattgta atgtaattgt tattatttta taaaaattaa tatgattctt 240
tgtgtttaag ttaattggag ggaacatata aaaagaattc tgtaaattta tagtgtataa 300
caatgtagat aaaatttttg aggagaagtt ttatctttga ctggaaagtt tgacttaaaa 360
ccgaaaattg atagaaaaaa tttagtgatt tgattttgtt ttcaaagtat tttaataatt 420
ttattatagc aatgtgttgt tactatattt aataaatgga caagcaataa gtattgttaa 480

```
attagtataa tggagcatta atagaagatt gcgagtaagg attagattaa tcctttttaa    540

tggaatggtt ttaacaaaag atgaagaaat actgattata atttttagtt ggatatgcgg    600

aagtaaaggg agaatctgag aaaagatttg acacttctat atgataattt gcatagttaa    660

tatttacata gagataagaa aaaataagat tatttttaaa tgaaaaatgg aggcaaaaat    720

aatatgaata aaaaagcata tggaaaagga gaagaattat ttactggagt tgttccaatt    780

cttgttgaat tagatggtga tgttaatgga cataaatttt ctgttagagg agagggtgaa    840

ggtgatgcta caaatggaaa acttacatta aaatttattt gtactactgg aaaattacct    900

gttccatggc caacattagt tactactttt gcttatggat tacaatgttt tgcaaggtat    960

ccagatcaca tgaaaagaca tgattttttt aagagtgcta tgccagaagg ttatgttcaa   1020

gaaagaacta tatcttttaa agatgatgga acatataaga caagagctga agttaagttt   1080

gaaggtgata cacttgttaa tagaatagag ttaaaaggta ttgattttaa agaagatgga   1140

aatattttag gacataaatt agaatataat tttaattcac ataatgtata tataacagca   1200

gataaacaaa agaatggaat aaaagctaat tttaaaatta gacataatgt tgaagatggt   1260

tctgttcaat tagcagatca ttatcaacaa aatactccaa ttggagatgg acctgttctt   1320

ttaccagata atcattattt atctacacaa tctgttttat ctaaagatcc aaatgaaaag   1380

agagatcaca tggtattatt agagtttgta actgctgctg gaattacaca tggaatggat   1440

gaattatata aaggaggttc tggaggttca ggacttgaac aacttgagag tataatcaat   1500

tttgaaaaat taactgaatg gacaagttct aatgttatgg aagagagaaa gataaaagtt   1560

tatttaccta gaatgaaaat ggaggaaaaa tataatttaa catctgtatt aatggctatg   1620

ggaattactg atgtttttag ttcttcagct aatctttctg gaatatcttc agcagagagt   1680

cttaagatat ctcaagctgt acatgcagca catgcagaaa taaatgaagc aggaagagaa   1740

gttgtaggat aagagctc                                                 1758
```

<210> SEQ ID NO 18
<211> LENGTH: 5367
<212> TYPE: DNA
<213> ORGANISM: Artificial Sequence
<220> FEATURE:
<223> OTHER INFORMATION: recombinant shuttle vector pMTL82151-ERM

<400> SEQUENCE: 18

```
cctgcaggat aaaaaaattg tagataaatt ttataaaata gttttatcta caattttttt     60

atcaggaaac agctatgacc gcggccgctg tatccatatg accatgatta cgaattcgag    120

ctcggtaccc ggggatcctc tagagtcgac gtcacgcgtc catggagatc tcgaggcctg    180

cagacatgca agcttggcac tggccgtcgt tttacaacgt cgtgactggg aaaaccctgg    240

cgttacccaa cttaatcgcc ttgcagcaca tccccctttc gccagctggc gtaatagcga    300

agaggcccgc accgatcgcc cttcccaaca gttgcgcagc ctgaatggcg aatggcgcta    360

gcataaaaat aagaagcctg catttgcagg cttcttattt ttatggcgcg ccgttctgaa    420

tccttagcta atggttcaac aggtaactat gacgaagata gcaccctgga taagtctgta    480

atggattcta aggcatttaa tgaagacgtg tatataaaat gtgctaatga aaaagaaaat    540

gcgttaaaag agcctaaaat gagttcaaat ggttttgaaa ttgattggta gtttaattta    600

atatattttt tctattggct atctcgatac ctatagaatc ttctgttcac ttttgttttt    660

gaaatataaa aaggggcttt ttagcccctt ttttttaaaa ctccggagga gtttcttcat    720

tcttgatact atacgtaact attttcgatt tgacttcatt gtcaattaag ctagtaaaat    780
```

```
caatggttaa aaaacaaaaa acttgcattt ttctacctag taatttataa ttttaagtgt    840
cgagtttaaa agtataattt accaggaaag gagcaagttt tttaataagg aaaaattttt    900
ccttttaaaa ttctatttcg ttatatgact aattataatc aaaaaaatga aaataaacaa    960
gaggtaaaaa ctgctttaga gaaatgtact gataaaaaaa gaaaaaatcc tagatttacg   1020
tcatacatag cacctttaac tactaagaaa aatattgaaa ggacttccac ttgtggagat   1080
tatttgttta tgttgagtga tgcagactta gaacatttta aattacataa aggtaatttt   1140
tgcggtaata gattttgtcc aatgtgtagt tggcgacttg cttgtaagga tagtttagaa   1200
atatctattc ttatggagca tttaagaaaa gaagaaaata aagagtttat atttttaact   1260
cttacaactc caaatgtaaa aagttatgat cttaattatt ctattaaaca atataataaa   1320
tcttttaaaa aattaatgga gcgtaaggaa gttaaggata taactaaagg ttatataaga   1380
aaattagaag taacttacca aaaggaaaaa tacataacaa aggatttatg gaaaataaaa   1440
aaagattatt atcaaaaaaa aggacttgaa attggtgatt tagaacctaa ttttgatact   1500
tataatcctc attttcatgt agttattgca gttaataaaa gttattttac agataaaaat   1560
tattatataa atcgagaaag atggttggaa ttatggaagt ttgctactaa ggatgattct   1620
ataactcaag ttgatgttag aaaagcaaaa attaatgatt ataaagaggt ttacgaactt   1680
gcgaaatatt cagctaaaga cactgattat ttaatatcga ggccagtatt tgaaattttt   1740
tataaagcat taaaaggcaa gcaggtatta gtttttagtg gatttttaa agatgcacac   1800
aaattgtaca agcaaggaaa acttgatgtt tataaaaaga aagatgaaat taaatatgtc   1860
tatatagttt attataattg gtgcaaaaaa caatatgaaa aactagaat aagggaactt   1920
acggaagatg aaaaagaaga attaaatcaa gatttaatag atgaaataga aatagattaa   1980
agtgtaacta tactttatat atatatgatt aaaaaaataa aaaacaacag cctattaggt   2040
tgttgttttt tattttcttt attaattttt ttaattttta gtttttagtt ctttttaaa   2100
ataagtttca gcctcttttt caatattttt taaagaagga gtatttgcat gaattgcctt   2160
ttttctaaca gacttaggaa atattttaac agtatcttct tgcgccggtg attttggaac   2220
ttcataactt actaatttat aattattatt ttcttttta attgtaacag ttgcaaaaga   2280
agctgaacct gttccttcaa ctagtttatc atcttcaata taatattctt gacctatata   2340
gtataaatat atttttatta tatttttact tttttctgaa tctattattt tataatcata   2400
aaaagtttta ccaccaaaag aaggttgtac tccttctggt ccaacatatt tttttactat   2460
attatctaaa taatttttgg gaactggtgt tgtaatttga ttaatcgaac aaccagttat   2520
acttaaagga attataacta taaaaatata taggattatc tttttaaatt tcattattgg   2580
cctccttttt attaaattta tgttaccata aaaaggacat aacgggaata tgtagaatat   2640
ttttaatgta gacaaaattt tacataaata taaagaaagg aagtgtttgt ttaaatttta   2700
tagcaaacta tcaaaaatta gggggataaa aatttatgaa aaaaaggttt tcgatgttat   2760
ttttatgttt aactttaata gtttgtggtt tatttacaaa ttcggccggc cgaagcaaac   2820
ttaagagtgt gttgatagtg cagtatctta aaattttgta taataggaat tgaagttaaa   2880
ttagatgcta aaaatttgta attaagaagg agtgattaca tgaacaaaaa tataaaatat   2940
tctcaaaact ttttaacgag tgaaaaagta ctcaaccaaa taataaaaca attgaattta   3000
aaagaaaccg ataccgttta cgaaattgga acaggtaaag ggcatttaac gacgaaactg   3060
gctaaaataa gtaaacaggt aacgtctatt gaattagaca gtcatctatt caacttatcg   3120
```

```
tcagaaaaat taaaactgaa tactcgtgtc actttaattc accaagatat tctacagttt   3180

caattcccta acaaacagag gtataaaatt gttgggagta ttccttacca tttaagcaca   3240

caaattatta aaaaagtggt ttttgaaagc catgcgtctg acatctatct gattgttgaa   3300

gaaggattct acaagcgtac cttggatatt caccgaacac tagggttgct cttgcacact   3360

caagtctcga ttcagcaatt gcttaagctg ccagcggaat gctttcatcc taaaccaaaa   3420

gtaaacagtg tcttaataaa acttacccgc cataccacag atgttccaga taaatattgg   3480

aagctatata cgtactttgt ttcaaaatgg gtcaatcgag aatatcgtca actgtttact   3540

aaaaatcagt ttcatcaagc aatgaaacac gccaaagtaa acaatttaag taccgttact   3600

tatgagcaag tattgtctat ttttaatagt tatctattat ttaacgggag gaaataattc   3660

tatgagtcgc ttttgtaaat ttggaaagtt acacgttact aaagggaatg tgtttaaact   3720

ccttttttgat aatctcatga ccaaaatccc ttaacgtgag ttttcgttcc actgagcgtc   3780

agaccccgta gaaaagatca aaggatcttc ttgagatcct ttttttctgc gcgtaatctg   3840

ctgcttgcaa acaaaaaaac caccgctacc agcggtggtt tgtttgccgg atcaagagct   3900

accaactctt tttccgaagg taactggctt cagcagagcg cagataccaa atactgttct   3960

tctagtgtag ccgtagttag gccaccactt caagaactct gtagcaccgc ctacatacct   4020

cgctctgcta atcctgttac cagtggctgc tgccagtggc gataagtcgt gtcttaccgg   4080

gttggactca agacgatagt taccggataa ggcgcagcgg tcgggctgaa cggggggttc   4140

gtgcacacag cccagcttgg agcgaacgac ctacaccgaa ctgagatacc tacagcgtga   4200

gctatgagaa agcgccacgc ttcccgaagg gagaaaggcg gacaggtatc cggtaagcgg   4260

cagggtcgga acaggagagc gcacgaggga gcttccaggg ggaaacgcct ggtatcttta   4320

tagtcctgtc gggtttcgcc acctctgact tgagcgtcga tttttgtgat gctcgtcagg   4380

ggggcggagc ctatggaaaa acgccagcaa cgcggccttt ttacggttcc tggccttttg   4440

ctggcctttt gctcacatgt tctttcctgc gttatcccct gattctgtgg ataaccgtat   4500

taccgccttt gagtgagctg ataccgctcg ccgcagccga acgaccgagc gcagcgagtc   4560

agtgagcgag gaagcggaag agcgcccaat acgcagggcc ccctgcttcg gggtcattat   4620

agcgattttt tcggtatatc catccttttt cgcacgatat acaggatttt gccaaagggt   4680

tcgtgtagac tttccttggt gtatccaacg gcgtcagccg ggcaggatag gtgaagtagg   4740

cccacccgcg agcgggtgtt ccttcttcac tgtcccttat tcgcacctgg cggtgctcaa   4800

cgggaatcct gctctgcgag gctggccggc taccgccggc gtaacagatg agggcaagcg   4860

gatggctgat gaaaccaagc caaccaggaa gggcagccca cctatcaagg tgtactgcct   4920

tccagacgaa cgaagagcga ttgaggaaaa ggcggcggcg gccggcatga gcctgtcggc   4980

ctacctgctg gccgtcggcc agggctacaa aatcacgggc gtcgtggact atgagcacgt   5040

ccgcgagctg gcccgcatca atggcgacct gggccgcctg ggcggcctgc tgaaactctg   5100

gctcaccgac gacccgcgca cggcgcggtt cggtgatgcc acgatcctcg ccctgctggc   5160

gaagatcgaa gagaagcagg acgagcttgg caaggtcatg atgggcgtgg tccgcccgag   5220

ggcagagcca tgactttttt agccgctaaa acggccgggg ggtgcgcgtg attgccaagc   5280

acgtccccat gcgctccatc aagaagagcg acttcgcgga gctggtgaag tacatcaccg   5340

acgagcaagg caagaccgat cgggccc                                     5367
```

<210> SEQ ID NO 19
<211> LENGTH: 4589

<212> TYPE: DNA
<213> ORGANISM: Artificial Sequence
<220> FEATURE:
<223> OTHER INFORMATION: recombinant shuttle vector DNA pMTL83151-ERM

<400> SEQUENCE: 19

```
cctgcaggat aaaaaaattg tagataaatt ttataaaata gttttatcta caattttttt     60
atcaggaaac agctatgacc gcggccgctg tatccatatg accatgatta cgaattcgag    120
ctcggtaccc ggggatcctc tagagtcgac gtcacgcgtc catggagatc tcgaggcctg    180
cagacatgca agcttggcac tggccgtcgt tttacaacgt cgtgactggg aaaaccctgg    240
cgttacccaa cttaatcgcc ttgcagcaca tccccctttc gccagctggc gtaatagcga    300
agaggcccgc accgatcgcc cttcccaaca gttgcgcagc ctgaatggcg aatggcgcta    360
gcataaaaat aagaagcctg catttgcagg cttcttattt ttatggcgcg ccgccattat    420
tttttgaac aattgacaat tcatttctta tttttatta agtgatagtc aaaaggcata    480
acagtgctga atagaaagaa atttacagaa aagaaaatta tagaatttag tatgattaat    540
tatactcatt tatgaatgtt taattgaata caaaaaaaaa tacttgttat gtattcaatt    600
acgggttaaa atatagacaa gttgaaaaat ttaataaaaa aataagtcct cagctcttat    660
atattaagct accaacttag tatataagcc aaaacttaaa tgtgctacca acacatcaag    720
ccgttagaga actctatcta tagcaatatt tcaaatgtac cgacatacaa gagaaacatt    780
aactatatat attcaattta tgagattatc ttaacagata taaatgtaaa ttgcaataag    840
taagatttag aagtttatag cctttgtgta ttggaagcag tacgcaaagg ctttttttatt    900
tgataaaaat tagaagtata tttatttttt cataattaat ttatgaaaat gaaagggggt    960
gagcaaagtg acagaggaaa gcagtatctt atcaaataac aaggtattag caatatcatt   1020
attgacttta gcagtaaaca ttatgacttt tatagtgctt gtagctaagt agtacgaaag   1080
ggggagcttt aaaaagctcc ttggaataca tagaattcat aaattaattt atgaaaagaa   1140
gggcgtatat gaaaacttgt aaaaattgca aagagtttat taaagatact gaaatatgca   1200
aaatacattc gttgatgatt catgataaaa cagtagcaac ctattgcagt aaatacaatg   1260
agtcaagatg tttacataaa gggaaagtcc aatgtattaa ttgttcaaag atgaaccgat   1320
atggatggtg tgccataaaa atgagatgtt ttacagagga agaacagaaa aaagaacgta   1380
catgcattaa atattatgca aggagcttta aaaaagctca tgtaaagaag agtaaaaaga   1440
aaaaataatt tatttattaa tttaatattg agagtgccga cacagtatgc actaaaaaat   1500
atatctgtgg tgtagtgagc cgatacaaaa ggatagtcac tcgcattttc ataatacatc   1560
ttatgttatg attatgtgtc ggtgggactt cacgacgaaa acccacaata aaaaaagagt   1620
tcggggtagg gttaagcata gttgaggcaa ctaaacaatc aagctaggat atgcagtagc   1680
agaccgtaag gtcgttgttt aggtgtgttg taatacatac gctattaaga tgtaaaaata   1740
cggataccaa tgaagggaaa agtataattt ttggatgtag tttgtttgtt catctatggg   1800
caaactacgt ccaaagccgt ttccaaatct gctaaaaagt atatcctttc taaaatcaaa   1860
gtcaagtatg aaatcataaa taaagtttaa ttttgaagtt attatgatat tatgtttttc   1920
tattaaaata aattaagtat atagaatagt ttaataatag tatatactta atgtgataag   1980
tgtctgacag tgtcacagaa aggatgattg ttatggatta taagcggccg gccgaagcaa   2040
acttaagagt gtgttgatag tgcagtatct taaaattttg tataatagga attgaagtta   2100
aattagatgc taaaaatttg taattaagaa ggagtgatta catgaacaaa aatataaaat   2160
```

-continued

```
attctcaaaa ctttttaacg agtgaaaaag tactcaacca aataataaaa caattgaatt   2220
taaaagaaac cgataccgtt tacgaaattg gaacaggtaa agggcattta acgacgaaac   2280
tggctaaaat aagtaaacag gtaacgtcta ttgaattaga cagtcatcta ttcaacttat   2340
cgtcagaaaa attaaaactg aatactcgtg tcactttaat tcaccaagat attctacagt   2400
ttcaattccc taacaaacag aggtataaaa ttgttgggag tattccttac catttaagca   2460
cacaaattat taaaaaagtg gtttttgaaa gccatgcgtc tgacatctat ctgattgttg   2520
aagaaggatt ctacaagcgt accttggata ttcaccgaac actagggttg ctcttgcaca   2580
ctcaagtctc gattcagcaa ttgcttaagc tgccagcgga atgctttcat cctaaaccaa   2640
aagtaaacag tgtcttaata aaacttaccc gccataccac agatgttcca gataaatatt   2700
ggaagctata tacgtacttt gtttcaaaat gggtcaatcg agaatatcgt caactgttta   2760
ctaaaaatca gtttcatcaa gcaatgaaac acgccaaagt aaacaattta agtaccgtta   2820
cttatgagca agtattgtct atttttaata gttatctatt atttaacggg aggaaataat   2880
tctatgagtc gcttttgtaa atttggaaag ttacacgtta ctaaagggaa tgtgtttaaa   2940
ctccttttg ataatctcat gaccaaaatc ccttaacgtg agttttcgtt ccactgagcg   3000
tcagaccccg tagaaaagat caaaggatct tcttgagatc cttttttct gcgcgtaatc   3060
tgctgcttgc aaacaaaaaa accaccgcta ccagcggtgg tttgtttgcc ggatcaagag   3120
ctaccaactc tttttccgaa ggtaactggc ttcagcagag cgcagatacc aaatactgtt   3180
cttctagtgt agccgtagtt aggccaccac ttcaagaact ctgtagcacc gcctacatac   3240
ctcgctctgc taatcctgtt accagtggct gctgccagtg gcgataagtc gtgtcttacc   3300
gggttggact caagacgata gttaccggat aaggcgcagc ggtcgggctg aacgggggt   3360
tcgtgcacac agcccagctt ggagcgaacg acctacaccg aactgagata cctacagcgt   3420
gagctatgag aaagcgccac gcttcccgaa gggagaaagg cggacaggta tccggtaagc   3480
ggcagggtcg gaacaggaga gcgcacgagg gagcttccag ggggaaacgc ctggtatctt   3540
tatagtcctg tcgggtttcg ccacctctga cttgagcgtc gatttttgtg atgctcgtca   3600
gggggcgga gcctatggaa aaacgccagc aacgcggcct ttttacggtt cctggccttt   3660
tgctggcctt ttgctcacat gttctttcct gcgttatccc ctgattctgt ggataaccgt   3720
attaccgcct ttgagtgagc tgataccgct cgccgcagcc gaacgaccga gcgcagcgag   3780
tcagtgagcg aggaagcgga agagcgccca atacgcaggg cccccctgctt cggggtcatt   3840
atagcgattt tttcggtata tccatccttt ttcgcacgat atacaggatt ttgccaaagg   3900
gttcgtgtag actttccttg gtgtatccaa cggcgtcagc cgggcaggat aggtgaagta   3960
ggcccacccg cgagcgggtg ttccttcttc actgtccctt attcgcacct ggcggtgctc   4020
aacgggaatc ctgctctgcg aggctggccg gctaccgccg gcgtaacaga tgagggcaag   4080
cggatggctg atgaaaccaa gccaaccagg aagggcagcc cacctatcaa ggtgtactgc   4140
cttccagacg aacgaagagc gattgaggaa aaggcggcgg cggccggcat gagcctgtcg   4200
gcctacctgc tggccgtcgg ccagggctac aaaatcacgg gcgtcgtgga ctatgagcac   4260
gtccgcgagc tggcccgcat caatggcgac ctgggccgcc tgggcggcct gctgaaactc   4320
tggctcaccg acgacccgcg cacggcgcgg ttcggtgatg ccacgatcct cgccctgctg   4380
gcgaagatcg aagagaagca ggacgagctt ggcaaggtca tgatgggcgt ggtccgcccg   4440
agggcagagc catgactttt ttagccgcta aaacggccgg ggggtgcgcg tgattgccaa   4500
gcacgtcccc atgcgctcca tcaagaagag cgacttcgcg gagctggtga agtacatcac   4560
```

```
cgacgagcaa ggcaagaccg atcgggccc                                       4589


<210> SEQ ID NO 20
<211> LENGTH: 6410
<212> TYPE: DNA
<213> ORGANISM: Artificial Sequence
<220> FEATURE:
<223> OTHER INFORMATION: recombinant shuttle vector pMTL84151-ERM

<400> SEQUENCE: 20

cctgcaggat aaaaaaattg tagataaatt ttataaaata gttttatcta caattttttt       60

atcaggaaac agctatgacc gcggccgctg tatccatatg accatgatta cgaattcgag      120

ctcggtaccc ggggatcctc tagagtcgac gtcacgcgtc catggagatc tcgaggcctg      180

cagacatgca agcttggcac tggccgtcgt tttacaacgt cgtgactggg aaaaccctgg      240

cgttacccaa cttaatcgcc ttgcagcaca tccccctttc gccagctggc gtaatagcga      300

agaggcccgc accgatcgcc cttcccaaca gttgcgcagc ctgaatggcg aatggcgcta      360

gcataaaaat aagaagcctg catttgcagg cttcttattt ttatggcgcg cccgccctta      420

agtctaaaaa ttaggggaga tgtaaggatt tgggaaaaat agaagatgtt ataatcataa      480

atatggtatt cgtaggctta aagtcaaaaa ggaggtgaaa tataaataga tttttagcta      540

aattaagtaa gaaataggag gagatttatt gaacaaaaaa ttagaaaaac catttgtata      600

taagagagag tacgatttga ctggatatga tgttgaaatt ttacaaaaat atgagttaga      660

acaagcaata tatgtttatg ttgggagtag ttgtgcatat aacatgagag ctagaagtag      720

taaatggaga taccatataa gaacaaataa taagtctata tgttgtaaca ttaaaaattt      780

tatacataac ttggaattgt tttataaaat ggaattaaag ttgtcagata atattattaa      840

tgataagcta tactatagca atatagcaga gtttgaagaa tttgaaacac tagaaaaagc      900

tagagaggta gaaagtacta ttataagtca atatcaattt ttagattcta taaatcacat      960

gttaaaacaa aaaataattt tattgagtaa taaggatagt gtgttaaaca taactaaaaa     1020

tggaaataca aattatttga aagtaaaaaa taaatacata gaaaaacata agaacaagcc     1080

aataatgaga taccatatca actgtcaatt caatacagat ggaagtgtca aaagtattac     1140

acaggagttt gaaccaatat tggaattaaa caaaaaaaat accctaagcc gaccaagcag     1200

agtattttta aaataatatt ttaagataac aacaaaatga gataatacta ctagacaatg     1260

acaactcaac taccaattga gtttatggag ctaccaactc caatatcggt ctaactgatt     1320

aagtatctgt agttatataa taatattgct atcaatttta gcatcttaac aatattatta     1380

tacatactaa gctaaaatta ttcaatagtt gtaaaagttg attagtcaat aagtatatat     1440

ttaatgtagt gttatctctt aaaaaaacta gataaggaga taataaatat atggaacaat     1500

tagattcaaa atataagttg aaaaaatttc taatggcagt atttagagat ggtataggac     1560

aaggaaataa tcttattgat aatgaatatg ttagagtatt tcaaaataat aaaagtaata     1620

gtaaacaatt agaactcgga gaagaattta aagaatatag taaaacaact ttttttaaaa     1680

atatagatga tatagtagaa tttaccttcg caaaaaatat ttattatgaa aatacatttt     1740

ttaacctatg tactactgat ggaaaagcag gaaccaatga aaacttaata aatagatatg     1800

cattaggatt tgattttgac aaaaaagaat taggacaagg ttttaattat aaagatataa     1860

ttaatttatt tactaagata ggattacatt atcatatcct agttgatagt ggaaatggat     1920

tccatgttta tgtgctaatt aataaaacta ataacattaa gttagtatca gaagttacaa     1980
```

-continued

```
atacattaat aaataaattg ggtgcagata aacaagcaaa tttatctact caagtattaa   2040
gagtacctta tacatataat attaaaaata ctactaaaca agtaaaaata atacaccaag   2100
acaaaaatat atatagatat gacatagaaa agttagctaa aaaatattgc aaagatgtaa   2160
aaacagtagg taatactaat acaaaatata tattagatag taagctacca aattgtatag   2220
tagatatttt aaaaaatggt agtaaagatg gacataaaaa cctagatttg caaaaaatag   2280
ttgtgacttt aagattgagg aataaaagtt taagtcaagt aatatccgtt gctagagaat   2340
ggaactatat atcacaaaat agtctttcaa atagtgagct agaatatcaa gtcaagtata   2400
tgtatgagaa acttaaaacg gttaattttg gttgtactgg ttgtgagttt aatagtgatt   2460
gttggaataa aatagaatca gattttatat atagtgatga agatactttg ttcaatatgc   2520
cacataagca ctcaaaggat ttgaaatata agaataggaa aggggttaaa ataatgactg   2580
gtaatcaatt gtttatctat aatgtgttac ttaacaataa agatagagaa ttaaacatag   2640
acgatataat ggagctgata acctataaac gtaagaagaa agttaaaaac attgttatga   2700
gtgaaaagac attaagagaa acattaaaag aacttcaaca taatgattat attacaaaaa   2760
caaaaggtgt tacaaagcta ggaataaaag atacatacaa tgtaaaagaa gttagatgta   2820
atatagataa acaatatact attagttact ttgttaccat ggcagtaatt tggggaataa   2880
tttcaactga agaattaaga ttatatactc acatgagata taagcaagat ttattggtca   2940
aagatgataa aataaaagga aatatattaa gaattaatca agaggaatta gcaaaagatt   3000
taggagtaac acagcaaaga atttcaaata tgatagaatc tttattagat actaaaattt   3060
tagatgtatg ggaaactaaa ataaatgata gaggatttat gtactataca tatagattaa   3120
acaagtagat ttttgatagg attagaattg attttctagt cctatttttta tgcaaaaaaa   3180
ctaattaata aaaatttctt ttggtaaaat aattgtacga gaattgcaaa aaaaaaatgg   3240
catcaaagta ttgaaattaa gccgttttaa aaatttcttt tggtaaaata attctacata   3300
tatatgtagt atatatatat atgtttttta gagaatgtat aactagaata tagagctaga   3360
atatagagaa tgtataacta gaatatagag ctagaatata gagaatgtat aactagaata   3420
tagagctaga atatagagaa tgtataacta gaatatagag ctagaatata gagaatgtat   3480
aactagaata tagagctaga atatagagaa tgtataacta gaatatagag ctagaatata   3540
gagaatgtat aactagaata tagagctaga atcctaatta gtaggtgctt ttttaaaaca   3600
agttaaaaat caaaaatagt attagtaagc attggaaatg ctagattcta aaatagaaaa   3660
gtaaaaaatt ggtgcactat ctaaacttat ctatatcgct ttttccgtcg tttggttctc   3720
tagttacgat acaggggata tgcttatatt gagttatagt actaatcagt gcttaatata   3780
gttaataaaa ttatagttac catagtttag taactatgat gtatgttagt tagaaacttg   3840
catttcggcc ggccgaagca aacttaagag tgtgttgata gtgcagtatc ttaaaatttt   3900
gtataatagg aattgaagtt aaattagatg ctaaaaattt gtaattaaga aggagtgatt   3960
acatgaacaa aaatataaaa tattctcaaa actttttaac gagtgaaaaa gtactcaacc   4020
aaataataaa acaattgaat ttaaaagaaa ccgataccgt ttacgaaatt ggaacaggta   4080
aagggcattt aacgacgaaa ctggctaaaa taagtaaaca ggtaacgtct attgaattag   4140
acagtcatct attcaactta tcgtcagaaa aattaaaact gaatactcgt gtcactttaa   4200
ttcaccaaga tattctacag tttcaattcc ctaacaaaca gaggtataaa attgttggga   4260
gtattcctta ccatttaagc acacaaatta ttaaaaaagt ggtttttgaa agccatgcgt   4320
ctgacatcta tctgattgtt gaagaaggat tctacaagcg taccttggat attcaccgaa   4380
```

```
cactagggtt gctcttgcac actcaagtct cgattcagca attgcttaag ctgccagcgg   4440

aatgctttca tcctaaacca aaagtaaaca gtgtcttaat aaaacttacc cgccatacca   4500

cagatgttcc agataaatat tggaagctat atacgtactt tgtttcaaaa tgggtcaatc   4560

gagaatatcg tcaactgttt actaaaaatc agtttcatca agcaatgaaa cacgccaaag   4620

taaacaattt aagtaccgtt acttatgagc aagtattgtc tatttttaat agttatctat   4680

tatttaacgg gaggaaataa ttctatgagt cgcttttgta aatttggaaa gttacacgtt   4740

actaaaggga atgtgtttaa actccttttt gataatctca tgaccaaaat cccttaacgt   4800

gagttttcgt tccactgagc gtcagacccc gtagaaaaga tcaaaggatc ttcttgagat   4860

cctttttttc tgcgcgtaat ctgctgcttg caaacaaaaa aaccaccgct accagcggtg   4920

gtttgtttgc cggatcaaga gctaccaact ctttttccga aggtaactgg cttcagcaga   4980

gcgcagatac caaatactgt tcttctagtg tagccgtagt taggccacca cttcaagaac   5040

tctgtagcac cgcctacata cctcgctctg ctaatcctgt taccagtggc tgctgccagt   5100

ggcgataagt cgtgtcttac cgggttggac tcaagacgat agttaccgga taaggcgcag   5160

cggtcgggct gaacgggggg ttcgtgcaca cagcccagct tggagcgaac gacctacacc   5220

gaactgagat acctacagcg tgagctatga gaaagcgcca cgcttcccga agggagaaag   5280

gcggacaggt atccggtaag cggcagggtc ggaacaggag agcgcacgag ggagcttcca   5340

gggggaaacg cctggtatct ttatagtcct gtcgggtttc gccacctctg acttgagcgt   5400

cgatttttgt gatgctcgtc aggggggcgg agcctatgga aaaacgccag caacgcggcc   5460

tttttacggt tcctggcctt ttgctggcct tttgctcaca tgttctttcc tgcgttatcc   5520

cctgattctg tggataaccg tattaccgcc tttgagtgag ctgataccgc tcgccgcagc   5580

cgaacgaccg agcgcagcga gtcagtgagc gaggaagcgg aagagcgccc aatacgcagg   5640

gccccctgct tcggggtcat tatagcgatt ttttcggtat atccatcctt tttcgcacga   5700

tatacaggat tttgccaaag ggttcgtgta gactttcctt ggtgtatcca acggcgtcag   5760

ccgggcagga taggtgaagt aggcccaccc gcgagcgggt gttccttctt cactgtccct   5820

tattcgcacc tggcggtgct caacgggaat cctgctctgc gaggctggcc ggctaccgcc   5880

ggcgtaacag atgagggcaa gcggatggct gatgaaacca agccaaccag gaagggcagc   5940

ccacctatca aggtgtactg ccttccagac gaacgaagag cgattgagga aaaggcggcg   6000

gcggccggca tgagcctgtc ggcctacctg ctggccgtcg gccagggcta caaaatcacg   6060

ggcgtcgtgg actatgagca cgtccgcgag ctggcccgca tcaatggcga cctgggccgc   6120

ctgggcggcc tgctgaaact ctggctcacc gacgacccgc gcacggcgcg gttcggtgat   6180

gccacgatcc tcgccctgct ggcgaagatc gaagagaagc aggacgagct tggcaaggtc   6240

atgatgggcg tggtccgccc gagggcagag ccatgacttt tttagccgct aaaacggccg   6300

gggggtgcgc gtgattgcca agcacgtccc catgcgctcc atcaagaaga gcgacttcgc   6360

ggagctggtg aagtacatca ccgacgagca aggcaagacc gatcgggccc              6410
```

<210> SEQ ID NO 21
<211> LENGTH: 3842
<212> TYPE: DNA
<213> ORGANISM: Artificial Sequence
<220> FEATURE:
<223> OTHER INFORMATION: recombinant shuttle vector pMTL85151-ERM

<400> SEQUENCE: 21

```
cctgcaggat aaaaaaattg tagataaatt ttataaaata gttttatcta caattttttt     60
atcaggaaac agctatgacc gcggccgctg tatccatatg accatgatta cgaattcgag    120
ctcggtaccc ggggatcctc tagagtcgac gtcacgcgtc catggagatc tcgaggcctg    180
cagacatgca agcttggcac tggccgtcgt tttacaacgt cgtgactggg aaaaccctgg    240
cgttacccaa cttaatcgcc ttgcagcaca tccccctttc gccagctggc gtaatagcga    300
agaggcccgc accgatcgcc cttcccaaca gttgcgcagc ctgaatggcg aatggcgcta    360
gcataaaaat aagaagcctg catttgcagg cttcttattt ttatggcgcg ccgcattcac    420
ttcttttcta tataaatatg agcgaagcga ataagcgtcg gaaaagcagc aaaaagtttc    480
ctttttgctg ttggagcatg ggggttcagg gggtgcagta tctgacgtca atgccgagcg    540
aaagcgagcc gaagggtagc atttacgtta gataaccccc tgatatgctc cgacgcttta    600
tatagaaaag aagattcaac taggtaaaat cttaatatag gttgagatga taaggtttat    660
aaggaatttg tttgttctaa tttttcactc attttgttct aatttctttt aacaaatgtt    720
cttttttttt tagaacagtt atgatatagt tagaatagtt taaaataagg agtgagaaaa    780
agatgaaaga aagatatgga acagtctata aaggctctca gaggctcata gacgaagaaa    840
gtggagaagt catagaggta gacaagttat accgtaaaca aacgtctggt aacttcgtaa    900
aggcatatat agtgcaatta ataagtatgt tagatatgat tggcggaaaa aaacttaaaa    960
tcgttaacta tatcctagat aatgtccact taagtaacaa tacaatgata gctacaacaa   1020
gagaaatagc aaaagctaca ggaacaagtc tacaaacagt aataacaaca cttaaaatct   1080
tagaagaagg aaatattata aaaagaaaaa ctggagtatt aatgttaaac cctgaactac   1140
taatgagagg cgacgaccaa aaacaaaaat acctcttact cgaatttggg aactttgagc   1200
aagaggcaaa tgaaatagat tgacctccca ataacaccac gtagttattg ggaggtcaat   1260
ctatgaaatg cgattaaggg ccggccgaag caaacttaag agtgtgttga tagtgcagta   1320
tcttaaaatt ttgtataata ggaattgaag ttaaattaga tgctaaaaat ttgtaattaa   1380
gaaggagtga ttacatgaac aaaaatataa aatattctca aaacttttta acgagtgaaa   1440
aagtactcaa ccaaataata aaacaattga atttaaaaga aaccgatacc gtttacgaaa   1500
ttggaacagg taaagggcat ttaacgacga aactggctaa aataagtaaa caggtaacgt   1560
ctattgaatt agacagtcat ctattcaact tatcgtcaga aaaattaaaa ctgaatactc   1620
gtgtcacttt aattcaccaa gatattctac agtttcaatt ccctaacaaa cagaggtata   1680
aaattgttgg gagtattcct taccatttaa gcacacaaat tattaaaaaa gtggtttttg   1740
aaagccatgc gtctgacatc tatctgattg ttgaagaagg attctacaag cgtaccttgg   1800
atattcaccg aacactaggg ttgctcttgc acactcaagt ctcgattcag caattgctta   1860
agctgccagc ggaatgcttt catcctaaac caaaagtaaa cagtgtctta ataaaactta   1920
cccgccatac cacagatgtt ccagataaat attggaagct atatacgtac tttgtttcaa   1980
aatgggtcaa tcgagaatat cgtcaactgt ttactaaaaa tcagtttcat caagcaatga   2040
aacacgccaa agtaaacaat ttaagtaccg ttacttatga gcaagtattg tctattttta   2100
atagttatct attatttaac gggaggaaat aattctatga gtcgcttttg taaatttgga   2160
aagttacacg ttactaaagg gaatgtgttt aaactccttt ttgataatct catgaccaaa   2220
atcccttaac gtgagttttc gttccactga gcgtcagacc ccgtagaaaa gatcaaagga   2280
tcttcttgag atcctttttt tctgcgcgta atctgctgct tgcaaacaaa aaaaccaccg   2340
ctaccagcgg tggtttgttt gccggatcaa gagctaccaa ctctttttcc gaaggtaact   2400
```

-continued

```
ggcttcagca gagcgcagat accaaatact gttcttctag tgtagccgta gttaggccac   2460

cacttcaaga actctgtagc accgcctaca tacctcgctc tgctaatcct gttaccagtg   2520

gctgctgcca gtggcgataa gtcgtgtctt accgggttgg actcaagacg atagttaccg   2580

gataaggcgc agcggtcggg ctgaacgggg ggttcgtgca cacagcccag cttggagcga   2640

acgacctaca ccgaactgag atacctacag cgtgagctat gagaaagcgc cacgcttccc   2700

gaagggagaa aggcggacag gtatccggta agcggcaggg tcggaacagg agagcgcacg   2760

agggagcttc cagggggaaa cgcctggtat ctttatagtc ctgtcgggtt tcgccacctc   2820

tgacttgagc gtcgattttt gtgatgctcg tcaggggggc ggagcctatg gaaaaacgcc   2880

agcaacgcgg cctttttacg gttcctggcc ttttgctggc cttttgctca catgttcttt   2940

cctgcgttat cccctgattc tgtggataac cgtattaccg cctttgagtg agctgatacc   3000

gctcgccgca gccgaacgac cgagcgcagc gagtcagtga gcgaggaagc ggaagagcgc   3060

ccaatacgca gggccccctg cttcggggtc attatagcga tttttcggt atatccatcc   3120

tttttcgcac gatatacagg attttgccaa agggttcgtg tagactttcc ttggtgtatc   3180

caacggcgtc agccgggcag gataggtgaa gtaggcccac ccgcgagcgg gtgttccttc   3240

ttcactgtcc cttattcgca cctggcggtg ctcaacggga atcctgctct gcgaggctgg   3300

ccggctaccg ccggcgtaac agatgagggc aagcggatgg ctgatgaaac caagccaacc   3360

aggaagggca gcccacctat caaggtgtac tgccttccag acgaacgaag agcgattgag   3420

gaaaaggcgg cggcggccgg catgagcctg tcggcctacc tgctggccgt cggccagggc   3480

tacaaaatca cgggcgtcgt ggactatgag cacgtccgcg agctggcccg catcaatggc   3540

gacctgggcc gcctgggcgg cctgctgaaa ctctggctca ccgacgaccc gcgcacggcg   3600

cggttcggtg atgccacgat cctcgccctg ctggcgaaga tcgaagagaa gcaggacgag   3660

cttggcaagg tcatgatggg cgtggtccgc ccgagggcag agccatgact tttttagccg   3720

ctaaaacggc cggggggtgc gcgtgattgc caagcacgtc cccatgcgct ccatcaagaa   3780

gagcgacttc gcggagctgg tgaagtacat caccgacgag caaggcaaga ccgatcgggc   3840

cc                                                                  3842
```

METHOD OF CULTURING SEGMENTED FILAMENTOUS BACTERIA IN VITRO

The present invention relates to an in vitro method for growing segmented filamentous bacteria (SFB). The present invention also relates to methods for genetically modifying a SFB strain.

Segmented filamentous bacteria (SFB) or *Candidatus arthromitus* or *Candidatus savagella* or *Arthromitus immunis* or *Arthromitus muris* are gram-positive anaerobic, clostridia-related, spore-forming commensals found in the gut (distal illeum) of many vertebrate species, including mouse, rat, rabbit, birds (e.g., chicken), fish, amphibian and probably humans (Klaasen et al., 1992; Yin et al., 2012). The size of the filament is comprised between 0.5 and 1000 μm in length. SFB produce intracellular offsprings (Schnupf et al., 2013; Ericsson et. al., 2014 for review). Intracellular offsprings once formed are unicellular until they start to filament and become bicellular, then tricellular.

SFB have garnered much interest because of their unique ability to educate the gut immune system and to induce a healthy state of physiological inflammation (Schnupf et al., 2013; Ivanov et al., 2009). SFB colonization leads to the maturation of the gut mucosal lymphoid tissue, induces a strong and broad IgA response, stimulates the T-cell compartment, upregulates intestinal innate defence mediators, and induce a striking increase in the small-intestinal Th17 responses (Schnupf et al., 2013; Ivanov et al., 2009; Gaboriau-Routhiau et al., 2009). In addition, SFB colonization exerts an adjuvant effect on systemic responses and can thus exacerbate pathologies in mouse models of encephalitis and arthritis, while protecting genetically predisposed mice against the development of type I diabetes (Lee et al., 2011; Wu et al., 2010; Chappert et al., 2013; Kriegel et al., 2011; Yurkovetskiy et al., 2013).

Unlike other commensals, the segmented filamentous bacterium intimately attaches to absorptive epithelial cells in the ileum and cells overlying Peyer's patches (Jepson et al., 1993; Chase et al., 1976). This colonization does not result in pathology; rather, it protects the host from pathogens (Ivanov et al., 2009).

The genomes of several SFB strains are known in the art. Recent sequencing of the rat and mouse SFB genomes revealed the highly auxotrophic needs of SFB and placed SFB between obligate and facultative symbionts (Pamp et al., 2012). These findings suggest that SFB obtain at least some of their nutritional requirements from their interaction with the host (Prakash et al., 2011; Sczesnak et al., 2011; Kuwahara et al., 2011; Pamp et al., 2012).

Yet, little is known about the segmented filamentous bacterium-host interaction that underlies the important immunostimulatory properties of the bacterium, because SFB have resisted in vitro culturing for more than 50 years.

Therefore, there is a need for an effective method of culturing SFB in vitro.

The inventors have grown mouse SFB outside their host in a segmented filamentous bacterium-host cell co-culturing system. The inventors have shown that in this system, single-celled SFB isolated from monocolonized mice undergo filamentation, segmentation, and differentiation to release viable infectious particles, the unicellular intracellular offspring, which can colonize mice to induce signature immune responses. The inventors have also observed in this co-culturing system the formation of SFB spores. In vitro, intracellular offspring can attach to mouse and human host cells and recruit actin. Further, SFB can potently stimulate the upregulation of host innate defence genes, inflammatory cytokines, and chemokines. These immunostimulatory properties of SFB increase host resistance to pathogens and can be exploited to direct immunity to particular pathogens of interest.

Accordingly, the present invention provides an in vitro method of culturing a segmented filamentous bacterium (SFB) strain, comprising co-culturing said segmented filamentous bacterium strain with a eukaryotic host cell, preferably mammalian host cell, more preferably human host cell, wherein the culture is performed at an $O_2$ level inferior to 5%, preferably inferior to 4%, in a rich tissue culture liquid medium containing bacterial medium components including iron, preferably at a concentration between 0.015 and 0.05 mM.

As used herein a segmented filamentous bacterium strain refers to a *Candidatus arthromitus* or *Candidatus savagella* or *Arthromitus immunis* or *Arthromitus muris* strain, preferably a *Arthromitus muris* strain.

Advantageously, the method comprises the steps of:

a) growing a eukaryotic host cell on a solid culture medium;

b) immerging the eukaryotic host cells grown in step a) in a eukaryotic host cell-SFB liquid culture medium;

c) challenging the cell culture of step b) with a SFB strain, preferably an intracellular SFB offspring;

d) co-culturing the live eukaryotic host cell and the SFB strain in the liquid culture medium at an $O_2$ level inferior to 5%, preferably inferior to 4%; and optionally e) recovering the cultured SFB strain.

With Regard to Step a):

The eukaryotic host cell can be any vertebrate cell, preferably any mammalian cell, more preferably any human or murine cell (e.g., a mouse cell).

In a preferred embodiment the eukaryotic host cell is an adherent cell in vitro. Advantageously, this adherent cell is able to differentiate and hence fares well under confluent conditions for extended periods of time in vitro.

In another preferred embodiment, the eukaryotic host cell is an epithelial cell. Advantageously, the eukaryotic host cell is a cell from the gastrointestinal tract, such as the colon or small intestine.

In another embodiment, the eukaryotic host cell is a cancer cell, preferably a carcinoma cell, more preferably an adenocarcinoma cell.

In a most preferred embodiment, the eukaryotic host cell is a mammalian gastrointestinal epithelial adherent cell or a mammalian adherent cancer cell, in particular a human or mouse colon epithelial or small intestine cell or a human or mouse adenocarcinoma cell.

In a particular embodiment, the eukaryotic host cell is selected from the group consisting of the human Caco-2, TC7 (which is a subclone of Caco-2) or HeLa cell lines or mouse mICcl2 or CMT93 cell lines, preferably the human Caco-2 or TC7 cell line.

Advantageously, the eukaryotic host cell is grown at an $O_2$ level between 0% (anaerobic conditions) and 5% (i.e., between 0 and 37.1 Torr), preferably between 0.5% and 3% (i.e., between 3.7 and 22.3 Torr), more preferably between 1 and 2.5% (i.e., between 7.4 and 18.6 Torr).

The humidity and temperature conditions for growing the eukaryotic host cell can be determined by routine tests by a person skilled in the art. The temperature is preferably between 36° C. and 38° C., more preferably 37 degrees Celcius.

The composition of the eukaryotic host cell culture medium can be determined by routine tests by a person skilled in the art. By way of example, the culture medium comprises Dulbecco's Modified Eagle Medium (DMEM) or Dulbecco's Modified Eagle Medium: Nutrient Mixture F-12 (DMEM/F12) advanced medium, inactivated (or decomplemented) fetal calf serum (FCS) and amino acids.

Advantageously, the eukaryotic host cell is grown until a cell confluence of at least 20%, and by order of increasing preference of at least 25%, 30%, 35%, 40%, 50%, 55%, 60%, 65%, 70%, 75%, 80%, 85%, 90%, 95%, 98%, and more preferably of 100%, is obtained.

In a preferred embodiment, the eukaryotic host cell is grown until a cell monolayer is obtained.

In another preferred embodiment, the eukaryotic host cells grown in step a) are plated on a plate, preferably on a tissue culture well or transwell, more preferably on a tissue culture transwell, prior to step b).

Advantageously, the seeding density of the eukaryotic host cell is between $1\times10^4$ and $6\times10^4$ cells per $cm^2$. By way of example the seeding density of the eukaryotic host cell is between $6\times10^4$ and $12\times10^4$ cells per culture well (i.e. per 3.8 $cm^2$) or $3\times10^4$ and $6\times10^4$ cells per culture transwell (i.e. per 1.12 $cm^2$).

Advantageously, when the SFB are added in step c), the culture density of the eukaryotic host cell is between $0.5\times10^5$ and $3\times10^5$ cells per $cm^2$. By way of example the culture density of the eukaryotic host cell is between $3\times10^5$ and $6\times10^5$ cells per culture well (i.e. per 3.8 $cm^2$) or $1\times10^5$ and $3\times10^5$ cells per culture transwell (i.e. per 1.12 $cm^2$).

With Regard to Step b):

The eukaryotic host cell-SFB liquid culture medium is a medium suitable for culturing both the eukaryotic host cell and the SFB strain.

Advantageously, said liquid culture medium is a rich tissue culture medium (e.g., DMEM/F12 advanced medium) containing bacterial medium components including iron.

Said liquid culture medium can comprise brain-heart infusion and a yeast/peptone/casein amino-acid mixture. These bacterial medium complements are well known in the art.

Iron can be in the ferrous form ($Fe^{2+}$ state) and/or ferric ($Fe^{3+}$ state). By way of example, iron can be in the form of $Fe^{2+}/Fe^{3+}$, $3\times Fe^{2+}$, $3\times Fe^{2+}$ or hemin, preferably $Fe^{2+}/Fe^{3+}$, $3\times Fe^{2+}$ or $3\times Fe^{2+}$.

Advantageously, iron concentration is between 0.015 and 0.05 mM, preferably between 0.02 and 0.04 mM.

In a preferred embodiment, said liquid culture medium comprises a medium for culturing the eukaryotic host cell, such as DMEM/F12 advanced medium, supplemented with fetal calf serum, non-essential amino acids (such as Glutamax™), 4-(2-hydroxyethyl)-1-piperazineethanesulfonic acid (HEPES), brain-heart infusion, a yeast/peptone/casein amino-acid mixture and iron.

The liquid culture medium can be supplemented with decomplemented fetal calf serum (FCS), in particular when the liquid culture medium comprises DMEM or DMEM/F12 advanced medium. Advantageously, the liquid medium is supplemented with 1% to 5% decomplemented FCS, preferably between 1% to 3%, more preferably 2%.

Advantageously, said liquid culture medium further comprises sugars, retinoic acid and/or nucleotides.

With Regard to Step c):

The SFB strain can be a wild-type strain or a genetically modified strain. A genetically modified SFB strain can be obtained from a wild-type SFB strain by transformation, transduction or conjugation.

The SFB strain can be in the form of a filament or an intracellular offspring.

The SFB strain can be isolated from a subject, in particular a mammal, such as a human or a mouse (e.g., a SFB monoassociated mouse). Methods for isolating a SFB strain from a mammal are known in the art (Lécuyer et al., 2014).

An individual SFB filament can be isolated by the following method: the ileal, caecal, and/or colonic contents from a subject is collected and the individual filament is captured using an inverted microscope and a micropipette attached to a micromanipulator.

An intracellular SFB offspring can be isolated under anaerobic or low aerobic conditions (i.e., between 0%-2% oxygen) by the following method: the ileal, caecal, and/or colonic contents from a subject is collected, filtered through a 100-μm mesh, separated from other faecal matter using a density gradient column and passed through a 5-μm filter to obtain a pure culture of unicellular intracellular offspring (average 0.7 μm). SFB filaments can also be collected on 5 μm filters following this method.

As used herein, the term "challenging" refers to the addition of a bacterium to an eukaryotic host cell regardless of whether this bacterium interacts (attaches/invades) or not the host cell.

In a preferred embodiment, the SFB strain is closely contacted with the eukaryotic host cell, preferably is in direct contact with the eukaryotic host cell.

As used herein, the term "closely contacted" refers to a co-culture of a eukaryotic host cell and a SFB strain wherein the distance between said eukaryotic host cell and said SFB strain is inferior or equal to 2 cm.

Advantageously, the seeding density of the SFB is between $0.2\times10^4$ and $10.10^4$ cells per $cm^2$. By way of example the seeding density of the SFB is between $1.10^4$ and $10.10^4$ bacteria per culture well (i.e. per 3.8 $cm^2$) or $1.10^4$ and $10.10^4$ bacteria per culture transwell (i.e. per 1.12 $cm^2$).

Advantageously, the ratio between the eukaryotic host cells and the SFB is between 0.1 and 100, preferably between 0.3 and 60.

With Regard to Step d):

The co-culture of the eukaryotic host cell and the SFB is performed at an $O_2$ level between 0% (anaerobic conditions) and 5%, preferably between 0.5 and 3%, more preferably between 1 and 2.5%.

The humidity and temperature conditions for co-culturing the live eukaryotic host cell and the SFB strain can be determined by routine tests by a person skilled in the art. The temperature is preferably between 36° C. and 38° C., more preferably 37° C.

The co-culture can be performed for 1, 2, 3, 4, 5 or 6 days.

The co-culture can also be performed until the SFB strain undergoes filamentation, segmentation, differentiation to release intracellular offsprings or spores.

Conditions to induce spore formation advantageously include adding a stress such as oxidative stress or short times of antibiotics (Davis and Savage, 1976).

With Regard to Step e)

The cultured SFB strain can be recovered in a form of a filament, an intracellular offspring or a spore.

A SFB filament can be recovered using an inverted microscope and a micropipette attached to a micromanipulator.

A SFB intracellular offspring can be recovered from a filament by filtration through a 5-μm filter. SFB filaments can be collected on 5 μm filters.

A SFB spore (that is a bacterial spore) can be recovered by a method well known in the art, such as the methods disclosed in International Application WO 2014/121298.

The present invention also provides the *Arthromitus muris* strain deposited by the Applicant, according to the Budapest Treaty, at CNCM (Collection Nationale de Cultures de Microorganismes, 25 rue du Docteur Roux, Paris) on Dec. 23, 2014, under the accession number CNCM 1-4932.

The present invention also provides a method for genetically modifying a segmented filamentous bacterium strain by conjugation, comprising the steps of:

i) genetically modifying an *Escherichia coli* strain with a recombinant shuttle vector DNA comprising a DNA sequence of interest to introduce in the SFB strain, wherein the said shuttle vector DNA is capable of replicating in the *E. coli* strain, and in the SFB strain to be targeted for genetic modification;

ii) co-culturing the genetically modified *E. coli* strain obtained in step i) together with the SFB strain to be targeted for genetic modification according to the in vitro method of culturing of the invention, wherein:

in step c) of said method of culturing of the invention, the cell culture of step b) is challenged with both the SFB strain to be targeted for genetic modification, preferably an intracellular SFB offspring, and said genetically modified *E. coli* strain; and in step d) of said method of culturing of the invention, the live eukaryotic host cell, the SFB strain and the genetically modified *E. coli* strain are co-cultured in the liquid culture medium at an $O_2$ level inferior to 5%;

iii) Recovering the Genetically Modified SFB Strain of Step ii).

The recombinant shuttle vector DNA can be a recombinant Clostridial shuttle vector DNA comprising a DNA sequence of interest and capable of replicating both in an *E. coli* strain and in a Clostridia strain. The construction of such a vector is known in the art (Heap et al., 2009).

Advantageously, the DNA sequence of interest can be under the control of a constitutive SFB, such as ribosomal, promoter for cytosolic expression or fused to a nucleotide sequence encoding a secreted lipoprotein for surface expression. By way of example, a strong promoter functional in SFB is the promoter of the SFB SFBNYU_003340 gene described by Yang et al. 2014.

The recombinant shuttle vector DNA can comprise one or different selectable antibiotic markers (i.e., antibiotic resistance cassettes). Any selectable antibiotic marker can be used, such as lincomycin, spectinomycin, thiamphenicol, chloramphenicol and tetracycline, preferably lincomycin. In in vitro SFB growth inhibition tests, SFB is sensitive to lincomycin at 0.1 ug/ml, spectinomycin at 4 ug/ml, thiamphenicol at 1 ug/ml, chloramphenicol at 5 ug/ml and tetracycline at 0.6 ug/ml. Advantageously, the recombinant shuttle vector DNA comprises a ERM/Lincomycin resistance cassette.

The DNA sequence of interest can be a DNA sequence encoding an antigen of interest. The DNA sequence encoding said antigen of interest is advantageously codon optimized for expression in SFB, e.g., following the method described by Sczesnak et al. 2011). By way of example, the antigen of interest can be IpaB or IpaD from *Shigella flexneri*, intimin and heat labile toxin from EPEC and the colonization factor antigen I (Cfa/I) adhesin CfaE from ETEC.

An example of a DNA sequence of interest under the control of the promoter of the SFB SFBNYU_003340 gene that has been codon optimized is provided in SEQ ID NO: 17. It encodes a Green Fluorescent Protein (GFP)-Ovalbumine (Ova) peptide fusion protein.

The *E. coli* strain can be a negatively-selectable auxotrophic *E. coli* strain (Danchin, 1977).

Advantageously, the *E. coli* strain requires diaminopimelic acid to grow. Such a strain can be selected against diaminopimelic acid in a rich culture medium.

The genetic modification of the *E. coli* strain can be carried out by electroporation, transduction, heat shock transformation or protoplast fusion.

The co-culturing of step ii) allows transferring the said shuttle vector DNA from the *E. coli* strain to the SFB by conjugation.

Advantageously, the cell culture of step b) is challenged first with the SFB strain to be targeted for genetic modification, and then with said genetically modified *E. coli* strain after there is outgrowth of the SFB strain.

The present invention also provides a method for genetically modifying a segmented filamentous bacterium strain by electroporation, comprising the steps of:

i) culturing and recovering a segmented filamentous bacterium strain according to the in vitro method of the invention;

ii) mixing the SFB strain recovered in step i) with a purified plasmid to be transformed, preferably in glycerol/$H_2O$ (e.g., 10% glycerol/$H_2O$);

iii) applying an electric pulse to the mixture obtained in step ii);

iv) recovering the genetically transformed SFB strain.

In step i) of this method, the SFB strain can be cultured for 2-4 days on TC7 cells.

In step i) of this method, the SFB strain can be recovered by collecting the SFB cell and putting it on ice under $O_2$ level between 0% (anaerobic conditions) and 5%, preferably between 0.5 and 3%, more preferably between 1 and 2.5%.

In step ii) of this method, the electric field is advantageously between 6 $kV.cm^{-1}$ and 30 $kV.cm^{-1}$, preferably between 6.5 $kV.cm^{-1}$ and 25 $kV.cm^{-1}$.

In step ii) the purified plasmid can be designed for use in Clostridia species (Heap et al., 2009). By way of example one can use the plasmid pMTL80110, pMTLP82254, pMTL83353, pMTL84422, pMTL85141, pMTL82151, pMTL83151, pMTL84151 or pMTL85151, all described by Heap et al., 2009 (also referred in GENBANK database under these accession numbers). Advantageously, the plasmid is selected from the group consisting of pMTL82151, pMTL83151, pMTL84151 and pMTL85151, further comprising an ERM/Lincomycin resistance cassette cloned between the FseI site and the PmeI site of the multiple cloning site of these plasmids. These plasmids are referred to as pMTL82151-ERM, pMTL83151-ERM, pMTL84151-ERM and pMTL85151-ERM, respectively described in SEQ ID NO: 18, 19, 20 and 21.

The plasmids can be purified by standard methods, mostly using commercially available kits such as Qiagen® plasmid purification kit for example.

In step iv), if the plasmid comprises an antibiotic resistance cassette then the SFB transformed with the plasmid is selected in vitro with the corresponding antibiotic marker.

The present invention also provides a method for genetically modifying a segmented filamentous bacterium strain by chemical transformation, comprising the steps of:

i) culturing and recovering a segmented filamentous bacterium strain according to the in vitro method of the invention;

ii) mixing the SFB strain recovered in step i) with a purified plasmid to be transformed, preferably in glycerol/calcium chloride (e.g., 10% glycerol/0.1M calcium chloride);

iii) incubating the mixture obtained in step ii);

iv) optionally applying a heat shock to the mixture;

v) recovering the genetically transformed SFB strain.

In step i) of this method, the SFB strain can be cultured for 2-4 days on TC7 cells.

In step i) of this method, the SFB strain can be recovered by collecting the SFB cell and putting it on ice under $O_2$ level between 0% (anaerobic condition) and 5%, preferably between 0.5 and 3%, more preferably between 1 and 2.5%.

In step iii), the SFB strain and the purified plasmid can be incubated for 15 to 45 min, preferably 30 min.

In step iv), the heat shocked is advantageously applied at 41-43° C., preferably at 42° C. for 15 to 45 seconds, preferably 30 seconds.

In step v), if the plasmid comprises an antibiotic resistance cassette then the SFB transformed with the plasmid is selected in vitro with the corresponding antibiotic marker.

The methods for genetically modifying a segmented filamentous bacterium strain according to the invention can further comprise a step of in vivo selecting the transformed SFB strain comprising: administrating (e.g., orally) the in vitro selected SFB transformed with a plasmid comprising an antibiotic resistance cassette into the gut of a mouse, then administrating to said mouse the corresponding antibiotic marker and then recovering the lived genetically transformed SFB strain from said mouse. The antibiotic marker (e.g., lincomycin) can be added to the drinking water of the mouse to be administered to said mouse. By way of example, lincomycin can be used in the drinking water at a low dilution, preferably between 50-500 μg/L.

A live genetically modified SFB strain can be used as an antigen delivery vehicle, either as filament, intracellular offspring or spore, preferably as a spore, after oral ingestion or parenteral administration to a subject, preferably a mammal.

Accordingly, the present invention also provides an isolated genetically modified SFB strain expressing an antigen of interest (e.g., IpaB or IpaD from *Shigella flexneri*, intimin and heat labile toxin from EPEC and the colonization factor antigen I (Cfa/I) adhesin CfaE from ETEC), preferably secreting said antigen or exposing said antigen on bacterium's surface.

The terms "a genetically modified SFB strain expressing an antigen of interest" and "a SFB strain genetically modified to express an antigen of interest" are used herein interchangeably.

As used herein, an antigen of interest refers to an (foreign) antigen derived from a microorganism or a cell (e.g., tumor cell) different from a SFB against which one intends to elicit an immune response in a subject. The microorganism can be a bacterium, virus or fungus organism. The cell is preferably of mammalian origin, preferably of human origin.

Given the potent ability of SFB to induce both B and T cell responses, including both Th1 and particularly Th17 cells, the antigen is advantageously selected to elicit a Th17 response.

Particular embodiments of the antigen include antigens derived from mainly surface proteins of the diarrheal pathogens *Shigella*, enterotoxic *Escherichia coli* (ETEC) or attaching and effacing lesion (A/E)-inducing enteropathogenic *E. coli* (EPEC). For a *Shigella* antigen, one can choose the type three secretion apparatus tip proteins IpaB and IpaD that are required for host cell invasion (Parsot 2009). IpaB and IpaD are conserved across different *Shigella* serotypes and, as recombinant proteins complexed with a double mutant heat-labile toxin, elicit a 90% protective efficacy to lethal pulmonary challenge of *Shigella* after intranasal immunization and a 40% protective efficacy when administered orally (Heine et al., 2013). In addition, IpaB-directed antibodies have been shown to inhibit *Shigella* plaque formation in vitro (Mills et al., 1988). For an ETEC antigen, one can choose the colonization factor antigen I (Cfa/I) adhesin CfaE that is located at the fimbrial tip and elicits protection from ETEC in a non-human primate *Aotus nancymaae* model after intradermal administration (Fleckenstein et al., 2014). As Cfa/I is only present in a subset of EPEC strains, it can be also include the heat-labile toxin (LT). The heat-labile toxin is highly immunogenic and a double-mutant of the toxin is used in vaccine research as a mucosal adjuvant (Martinez-Becerra et al., 2012). However, as SFB already has strong immunostimulatory potential, only the nontoxic B subunit of LT (LTB) that can by itself elicit protective antibody responses to the toxin when expressed cytosolically or surface localized by *Bacillus subtilis* can be selected (Paccez et al., 2007). For an EPEC antigen, one can choose the adhesin intimin. Intimin mediates the characteristic formation of the attaching and effacing (A/E) lesions by binding to the translocated receptor Tir (Kaper et al., 2004) and is found in both typical and atypical EPEC, in enterohaemorrhagic *E. coli* and the murine EPEC-like strain *C. rodentium*. Intimin as a protective immunogen has been validated in a number of animal models of infection with rabbit EPEC, EHEC and *C. rodentium* (Ferreira et al., 2011). Specifically it can be chosen a fragment encoding amino acids 363 to 808 of the 94 kDa beta-intimin antigen, the most frequent EPEC intimin subtype in human EPEC diarrheal cases and the subtype present in *C. rodentium*. This fragment can elicit protective immunity when given as a subcutaneous subunit vaccine or when delivered orally or sublingually by an intimin fragment-expressing *Lactobacillus* strain and shows promise in inducing intimin type-independent immunity (Ferreira et al., 2008 and 2011, Ghaem-Maghami, M. et al., 2001).

The genetically modified SFB strain can be obtained by transformation, transduction or conjugation as described above, preferably by a method for genetically modifying a segmented filamentous bacterium strain according to the invention.

The present invention also provides a live genetically modified SFB strain expressing an antigen of interest as defined above for use as a medicament, in particular for use in preventing or treating a disease caused by a microorganism from which said antigen derives, or a cancer.

Said SFB strain can be in the form of a filament, an intracellular offspring or a spore, preferably a spore.

The present invention also provides a therapeutic immunogenic (or vaccine) composition comprising a live genetically modified SFB strain expressing an antigen of interest as defined above.

Said SFB strain can be in the form of a filament, an intracellular offspring or a spore, preferably a spore.

The terms "immunogenic composition" and "vaccine composition" are used interchangeably herein.

The present invention also provides an immunogenic composition as described above for use in preventing or treating a disease caused by a microorganism from which said antigen derives or a cancer.

The genetically modified SFB strain expressing an antigen of interest and the immunogenic composition comprising the said genetically modified SFB strain according to the present invention are particularly suitable for eliciting in a subject antibodies directed to said antigen.

Advantageous said immunogenic composition comprises a pharmaceutically acceptable carrier.

As used herein, a "pharmaceutically acceptable carrier" includes any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field.

The genetically modified SFB strain expressing an antigen of interest and the immunogenic composition comprising the said genetically modified SFB strain according to the present invention are administered to a mammal subject, preferably a human, in an amount sufficient to prevent or attenuate the severity, extent of duration of the infection by the microorganism from which said antigen derives or a cancer.

The therapeutically effective amount varies depending on the subject being treated, the age and general condition of the subject being treated, the capacity of the subject's immune response to synthesize antibodies, the degree of protection desired, the severity of the condition to be treated, and its mode of administration, among other factors. An appropriate effective amount can be readily determined by one of skill in the art. A therapeutically effective amount will fall in a relatively broad range that can be determined through routine trials.

Following an initial vaccination, the subject may receive one or two booster injections at an appropriate interval determined by one of skill in the art.

Typically, the immunogenic composition is prepared as an injectable form (either a liquid solution or suspension) or as a solid form suitable for solution or suspension in a liquid carrier prior to injection.

Once formulated, the immunogenic composition may be administered parenterally or by mucosal routes, preferably orally.

The present invention also provides the use of a genetically modified SFB strain expressing an antigen of interest or an immunogenic composition as defined above for the manufacture of a medicament, preferably of a preventive or therapeutic vaccine against a microorganism from which said antigen derives in a subject or a cancer.

The present invention also provides a method for preventing and/or treating a infection caused by a microorganism from which said antigen derives or a cancer, comprising administering to a subject in need thereof a genetically modified SFB strain expressing an antigen of interest or an immunogenic composition as defined above, in an amount effective to inhibit said microorganism infection of susceptible cells so as to thereby prevent or treat the infection or to inhibit the growth of cancer cells so as to thereby prevent or treat cancer.

The term "treating" includes the administration of a genetically modified SFB strain expressing an antigen of interest or an immunogenic composition as defined above to a patient who has an infection, a symptom of infection or a cancer, with the purpose to cure, heal, alleviate, relieve, alter, remedy, ameliorate, improve, or affect the infection and/or the symptoms of the infection, or the cancer.

The term "preventing" means that the progression of an infection is reduced and/or eliminated, or that the onset of an infection or cancer is delayed or eliminated.

The present invention also provides the use of a SFB strain obtainable by the in vitro method of culturing of the invention, as a probiotic.

Said SFB strain can be alive or dead, preferably alive.

Said SFB strain can be in the form of a filament, an intracellular offspring or a spore, preferably a spore.

The present invention also provides a food product (e.g., dairy product) comprising a SFB strain obtainable by the in vitro method of culturing of the invention.

Said SFB strain can be alive or dead, preferably alive.

Said SFB strain can be in the form of a filament, an intracellular offspring or a spore, preferably a spore.

In addition to the preceding features, the invention further comprises other features which will emerge from the following description, which refers to examples illustrating the present invention, as well as to the appended figures.

EXAMPLE 1

Figure 1:
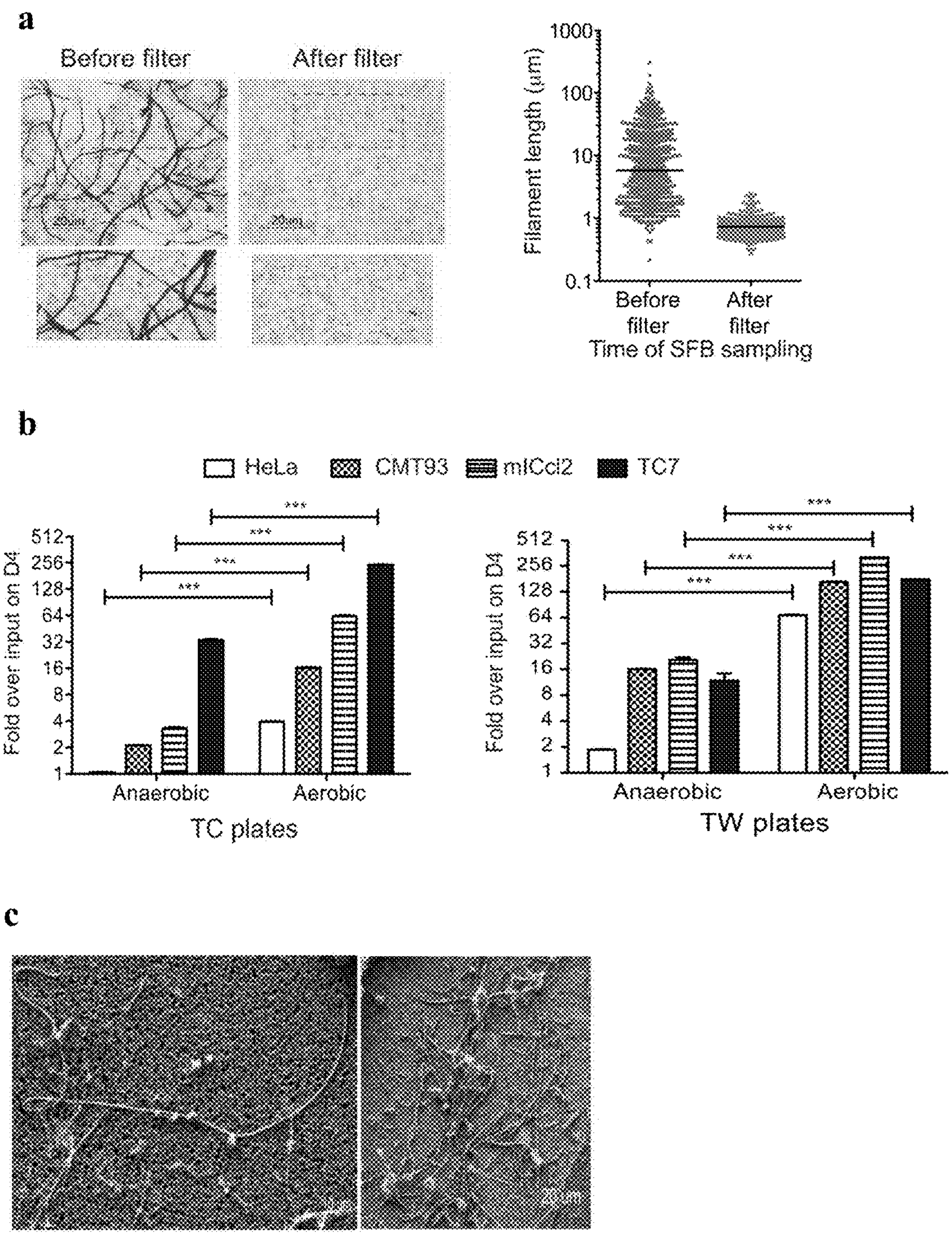
FIG. 1: Growth and growth requirements of SFB in vitro. a, Gram stain and length of SFB before and after 5-μm filtration; b, qPCR of SFB growth on host cells at the indicated conditions; c, SEM images of 4-day-old SFB filaments grown anaerobically on TC7 cells on transwells; d-i, SFB growth at low oxygen concentrations (d), on the indicated cell line seeded on transwells; e, on TC7 cells at indicated cell confluence; f, g, under various b, i, h, Statistical analysis using the two-tailed ttest (*P=<0.05, P=<0.01, *P=<0.001).
Figure 1:
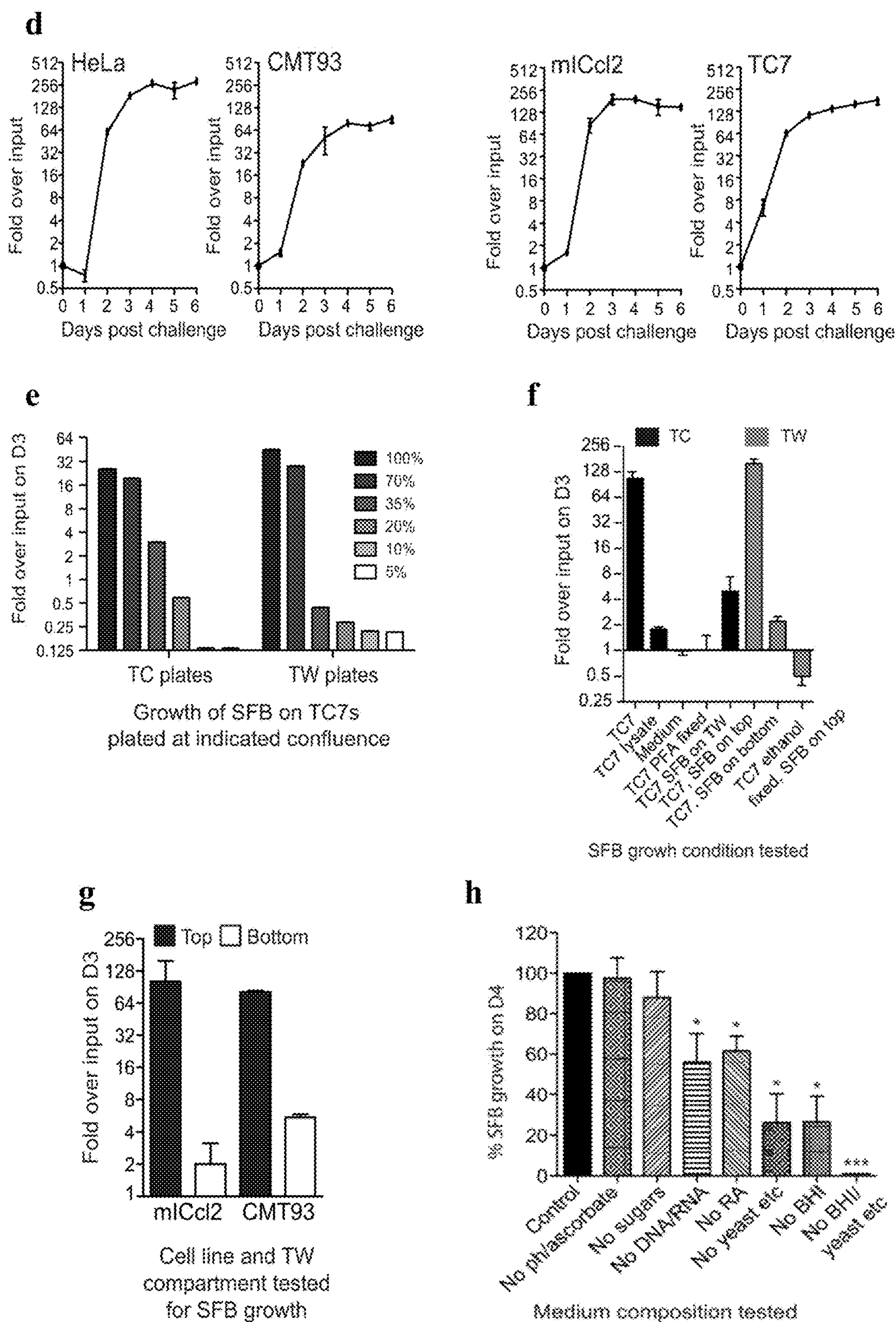
Figure 1:
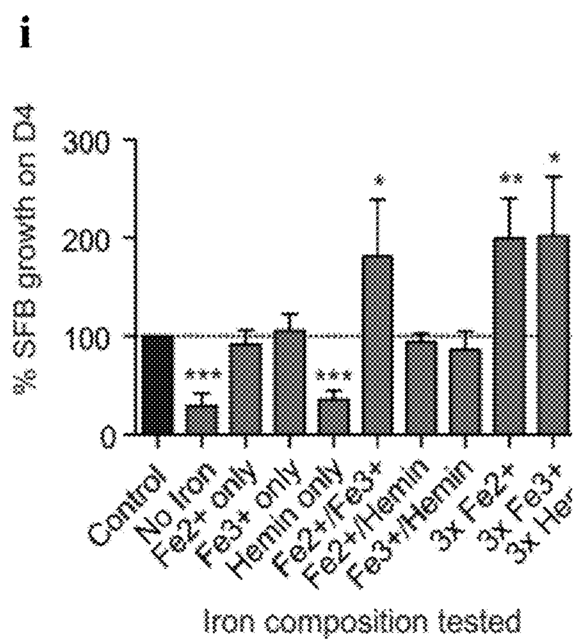

Growth and Host Interaction of Mouse Segmented Filamentous Bacteria in Vitro Materials and Methods Cell Culture and SFB-specific Culture Medium TC7, CMT93, and HeLa cells were cultured in DMEM (Gibco 31885) with 10% inactivated fetal calf serum (FCS; AbCys CVFSVF00-0U) and non-essential amino acids (Invitrogen 11140-035). mICcl2 were maintained in DMEM/F12 advanced medium (Gibco 12634) with 2% inactivated FCS and Glutamax (Gibco 35050) and supplemented with 10 nM hEGF (Sigma E9644), 50 nM dexamethasone (Sigma D4902) and 1 nM triiodothyronine (Sigma T5516). HeLa cells were obtained from ATCC. All cell lines were tested for *mycoplasma* every 2 weeks and always found to be negative. Cells were plated either on regular 12-well tissue culture plates or on Costar transwell plates with 0.4-μm filters (Sigma CLS3460 and Fisher Scientific W2127P) from 1 to 3 days before the experiment such that a monolayer was present at the start of the experiment and added to a low oxygen chamber overnight for slowly lowering oxygen concentrations in the medium of the cells. At the start of SFB culturing, the TC7, CMT93, HeLa and mICcl2 medium is first replaced with (equilibrated: 1% oxygen) medium before SFB addition (directly to the TC7 cells).

SFB medium was made up as follows: DMEM/F12 advanced medium with 2% FCS, Glutamax and 12.5 mM HEPES (Sigma H0887) with the following supplementation: 1 in 100 dilution of (1) brain-heart infusion (BD Difco 237500) 5× concentrated, (2) peptone/yeast (BBL Biosafe 211862) at 10% and casein amino acids at 5% (DIFCO 0320-01-1), (3) ribose/cellobiose/mannose (Sigma: R9629, C7252, M6020) at 200 mM; 1 in 1,000 dilution of (1) ferrous sulphate (Merck 3965) at 10 mM, (2) ferric ammonium citrate (LabGuard 0658) at 12.5 mM, (3) Hemin (Sigma 51280) at 1.5 mM in 50% ethanol with 1.4 N $NH_4OH$, (4) sodium ascorbate at 10 mg $ml^{-1}$ with 1-phosphoascorbate at 500 mM (Sigma: A4034, 49752); 1 in 10,000 dilution of retinoic acid (Sigma R2625) at 30 mg $ml^{-1}$ in DMSO; 1 in 500 dilution of (1) sperm DNA (Life Technologies 15632-011) at 10 mg $ml^{-1}$ digested for 1 h with 10 μl DNaseI (Roche 04 716 728 001) at 37° C. and heat inactivated at 75° C. for 30 min, (2) RNA at 10 mg $ml^{-1}$ (Sigma R6750) undigested. SFB medium specific medium supplements, except for the nucleotides and hemin were prepared fresh every 2 weeks and otherwise stored at 4 or −20° C. for retinoic acid, and nucleotides. When mICcl2 cells were used, SFB medium was further supplemented with hEGF, dexamethasone, and triiodothyronine. Notably, additional supplementation with 0.2% yeast extract (BD 212750; 1/100 from 20%) further improves SFB growth and it is not necessary to add ascorbate, phosphoascorbate or hemin.

Purification of Intracellular Offspring from SFB-monoassociated Mice and Infection Protocol All liquids used for the isolation of intracellular offspring were pre-equilibrated overnight in an anaerobic chamber set to 0% oxygen. SFB-monoassociated $JH^{-/-}$ mice were killed aseptically in a tissue culture hood and then placed in an anaerobic cabinet for dissection. The ileal, caecal, and colonic contents were resuspended in 50 ml PBS and homogenized by vortexing. Homogenates were passed through a 100-μm mesh to remove large faecal debris. The filtrate was spun at 8,000 g for 5 min to pellet bacteria and insoluble material, and the pellet was resuspended in 3 ml PBS per mouse killed, layered onto 3 ml 50% and 2 ml 30% Nycodenz (AbCYS 1002424) solution made with PBS in 15 ml Falcon tubes and spun for 10 min at 4,000 g. SFB within the 30% fraction were collected, diluted in PBS, and bacteria were pelleted for 10 min at 8,500 g. Pellets were resuspended in 15 ml pre-equilibrated PBS by pipetting/vortexing and filtered through a 5-μm filter (Sigma Z612502). The filtrate was again centrifuged for 5 min at 8,000 g and the pellet was resuspended in an appropriate amount of pre-equilibrated culture medium. Usually one mouse was killed for every four 12-well plates used, and 50 μl of bacterial suspension was added to each well. To facilitate adhesion, cells challenged with SFB were sealed in ziplock bags within the cabinets, removed from the cabinet, and spun for 10 min at 300 g.

SFB are allowed to grow in the presence of eukaryotic cells for 3 days during which the oxygen concentration is increased incrementally from 1% on day 0 to 1.5% on day 1, to 2% on day 2, and to 2.5% on day 3. Subcultures can be prepared on day 3 by taking aliquots of the culture supernatant and using this to challenge freshly prepared eukaryotic cells (prepared as described above on transwell filters and at low oxygen conditions).

SFB Recovery, and Quantification and Analysis of SFB Growth

To recover SFB, the culture supernatant was collected and centrifuged for 4 min at 8,000 g and the pellet was resuspended in 100 μl PBS, of which 20 μl was spotted on glass slides for the Gram stain, 30 μl was mixed with an equal volume of 50% glycerol and frozen at −80° C., and the remaining 50 μl was used for DNA extraction. The DNA was isolated with a Qiagen stool kit (51504; without the use of the inhibitor tablet) and diluted 1 in 20. SFB growth was enumerated by qPCR analysis of the 16S rRNA genes using the following primer pairs: the SFB specific F: 5'-AGGAGGAGTCTGCGGCACATTAGC-3' (SEQ ID NO: 1); and the universal R: 5'-TCCCCACTGCTGCCTCCCGTAG-3' (SEQ ID NO: 2). For qPCR, 6 μl of diluted SFB DNA was mixed with 1.5 μl of a 4 mM primer mix and 7.5 μl of Power SybrGreen Master mix (Applied 4368708) and run on an ABI 7900HT machine in a 384-well plate. Statistical analysis used a two-tailed Student's t-test (*P=<0.05, P=<0.01, *P=<0.001). SFB segment length analysis used ImageJ. For SEM analysis, SFB-containing supernatants were washed with PBS and suctioned onto 0.1-μm filters (Watman 110405) and fixed in 0.1 M cacodylate buffer containing 2.5% glutaraldehyde before being processed. Cells for SEM were fixed in PHEM buffer (18.14 g PIPES, 6.5 g HEPES, 3.8 g EGTA, 0.99 g MgSO4 per litre with 10 M KOH to pH 7.0) containing 4% sucrose and 2.5% glutaraldehyde, and processed for SEM. For fluorescence, cells were fixed in PBS/3.7% PFA, permeabilized with PBS/0.1% Triton X-100, stained with DAPI and A568-phalloidin, and stacks of 0.4-μm slices were taken on a Leica SP5 confocal microscope.

Colonization of Germ Free Mice with In Vitro-grown SFB

This experiment was done independently twice with similar results; one experiment is shown. SFB grown in vitro for 3 days on TC7 and mICcl2 cells on transwells were divided in equal parts and one half was filtered through a 5-μm filter to obtain a fraction containing intracellular offspring only. Bacteria were concentrated by centrifugation to obtain 0.25 ml of bacteria in PBS per mouse. The number of animals used followed availability of animals, isolators, and input quantities. Randomization or blinding was otherwise not performed. Two groups of four 11-week-old C57BL/6 male and female mice maintained at the germ-free facility were starved for one night, gavaged with 0.25 ml 400 mM sodium bicarbonate, followed by 0.25 ml of in vitro-grown SFB. Age-matched control mice were colonized with in vivo-derived SFB as described below. Faecal samples were collected for each mouse at various times during a 3 week period, SFB DNA was extracted using a Qiagen stool kit and quantified on the basis of qPCR analysis of 16S rDNA and comparison with a SFB DNA sample of known SFB genome concentration as determined by Illumina sequencing. To monitor SFB associated with the ileum, DNA was extracted from frozen ileal biopsies using the method in Godon et al., 1997.

Isolation and Staining of Lamina Propria Lymphocytes from C57BL/6 Mice

Age-matched germ-free B6 mice and mice colonized with either in vitro- or in vivo-grown SFB for 3 weeks were analysed for their innate and adaptive immune response as described in Ivanov et al., 2009. Briefly, after excision of Peyer's patches, the mouse small intestine was washed in PBS, and ileal samples were placed in RNAlater for RNA extraction, complementary DNA (cDNA) synthesis, and qPCR analysis using SYBR or Taqman technologies (Applied Biosystems) and a QuantStudio7 qPCR machine. Values were normalized to TfrC.

Lamina propria lymphocytes (LPL) were prepared as previously described by Gaboriau-Routhiau et al., 2009. The remaining small intestine was incubated four times in 60 ml of PBS-3 mM EDTA (Sigma) for 10 min at 37° C., and digested in 60 ml of RPMI 1640 with 20% FCS (Gibco), 100 U $ml^{-1}$ collagenase (Sigma), and 175 U $ml^{-1}$ DNase I (Sigma) for 40 min at 37° C. LPL were then purified on a 40-80% Percoll gradient run for 15 min at 2,000 g and resuspended in DMEMGlutamax with 8% FCS, 1 mM HEPES, 0.02 mM folic acid, 0.67 mM L-arginine, and 0.27 mM L-asparagine (all from Sigma).

Analysis of LPL for surface antigens and intracellular expression of IL-17 and IL-10 was by flow cytometry as described 5. Briefly, LPL were stimulated for 4 h with 100 ng $ml^{-1}$ phorbol 12-myristate 13-acetate and 1 μg $ml^{-1}$ ionomycin, in the presence of Brefeldin A (10 μg $ml^{-1}$) (all from Sigma). Cells used for surface analysis were left unstimulated. For surface staining, LPL were labelled for 20 min at 4° C. with a cocktail of the following antibodies: FITC-anti-GL7 (clone GL7), PerCP-anti-CD8a (clone 53-6.7), APC-H7-anti CD4 (clone GK1.5), AF647-anti-B220 (clone RA3-6B/2) (all from BD Pharmingen), PE-anti-IgA (Southern Biotech), and eFluor450-anti-CD45 (clone 30-F11) and PECy7-anti-CD3 (clone 145-2C11) (both from eBioscience).

For intracellular cytokine staining, cells were further fixed in 2% PFA for 20 min at room temperature (~24° C.), and washed and stained overnight at 4° C. with PE-anti-IL-17 (clone TC11-18H10) and APC-anti-IL-10 (clone JES5-16E3) (BD Pharmingen) diluted in PBS-1% FCS-0.5% saponin (Sigma). Labelled cells were analysed with a FACSCanto II and FACSDiva software (BD Biosciences). Gates were set on living cells after Aqua live/dead dye exclusion (Invitrogen).

For qPCR analysis, the median value of germ-free mice was calculated and used as the reference value of 1 for comparison of the median value of the test samples.

Colonization of Germ-free Mice with SFB from Faeces and *E. coli*

Germ-free male and female C3H/HeN mice were obtained from INRA (ANAXEM platform) germ-free facilities. Eight- to nine-week-old germ-free mice were gavaged with 0.5 ml of either fresh anaerobic cultures of *E. coli* MG1655 or faecal homogenate from SFBmonoassociated mice (Ivanov et al., 2009). Colonization by SFB was monitored in faeces through bacterial DNA extraction and 16S rDNA amplification by qPCR using specific primer pairs for SFB. Values were normalized to Ccl25, a constitutively expressed epithelial cell marker, and compared with the median value from germ-free control mice. Germ-free and gnotobiotic mice were maintained in plastic isolators and fed ad libitum on a commercial diet sterilized by γ-irradiation (40 kGy). The numbers of animals used followed availability of animals, isolators, and were obtained from two independent experiments. Randomization or blinding was otherwise not performed. Gnotobiotic mice were killed on day 21 after colonization in parallel with age-matched germ-free controls. All animal procedures were performed in accordance with French legislation and EEC regulations for the care and use of laboratory animals, approved by the local ethics committee and authorized by the French Ministry of Research.

Host Response In Vitro to SFB Growth and MAMP Stimulation

Host response to SFB and MAMPs included pooled results from four independent experiments with three technical samples. Generally a minimum of triplicate biological replicates were used and increased if trends were clear but significance not. After 3 days of in vitro growth of SFB on either mICcl2 or TC7 cells on transwells in SFB medium lacking hemin and sodium ascorbate, at 1-2.5% oxygen, cells were lysed and RNA was extracted using a Nucleospin RNA kit (Macherey-Nagel). cDNA was synthesized using RNA superscript II, oligo dT, RNaseout, and dNTPs (Invitrogen), and pPCR was performed on an ABI 7900HT and QuantStudio7 (Life Technologies) qPCR machine using the protocol described by Schnupf et al., 2012. TaqMan assays were performed as suggested by the supplier. Values were normalized to B2M and Ct values for Reg3γ, Tnfα, and Fabp2 were set to 41 in control cells owing to the lack of transcript detection. MAMP stimulation used the following agonists at the highest concentrations recommended by the supplier (Invivogen): Pam2CSK4 (tlrlpm2 s-1) at 100 ng $ml^{-1}$, Pam3CSK4 (tlrl-pms) at 300 ng $ml^{-1}$, peptidoglycan of *E. coli* K12 (Tlr-ksspgn) at 10 μg $ml^{-1}$, MDP (tlrl-mdp) at 10 μg $ml^{-1}$, CpG (ftr-1584) at 3 μg $ml^{-1}$, flagellin (tlrl-pstfla-5) at 100 ng $ml^{-1}$. Excess for flagellin (10×) was also tested and found to be similar.

Mouse and Human qPCR Primers Used

Mouse Taqman® Assays:

B2M Mm00437762_m1, TfrC Mm00441941_m1, Ccl25 Mm00436443_m1, Fabp2 Mm00433188_m1, Reg3 g Mm01181783_g1, Fut2 Mm00490152_S1, Aqp3 Mm01208559_m1, Pigr Mm00465049_m1, Ltf Mm00434787_m1, Tff3 Mm00495590_m1, Tnfa Mm00443258_m1, IL1a Mm00439620_m1, IL1b Mm00434228_m1, IL6 Mm00446190_m1, IL15 Mm00434210_m1, IL18 Mm00434225_m1, Cxcl2 Mm00436450_m1, Ccl2 Mm00436450_m1, Ccl5 Mm01302428_m1, Ccl7 Mm01308393_g1, Ccl20 Mm01268754_m1, Ccl28 Mm00445039_m1, Csf2 Mm01290062_m1

Mouse Sybr® Primers

```
B2M:
                                    (SEQ ID NO: 3)
F: tcagtcgtcagcatggctcgc;

                                    (SEQ ID NO: 4)
R: tccggtgggtggcgtgagtatac

iNos:
                                    (SEQ ID NO: 5)
F: cagctgggctgtacaaacctt;

                                    (SEQ ID NO: 6)
R: cattggaagtgaagcgtttcg

Saa1:
                                    (SEQ ID NO: 7)
F: catttgttcacgaggcatcc;

                                    (SEQ ID NO: 8)
R: gtttttccagttagcttccttcatgt

Saa2:
                                    (SEQ ID NO: 9)
F: tgtgtatcccacaaggtttcaga;

                                   (SEQ ID NO: 10)
R: ttattaccctctcctcctcaagca

Saa3:
                                   (SEQ ID NO: 11)
F: cgcagcacgagcaggat;

                                   (SEQ ID NO: 12)
R: ccaggatcaagatgcaaagaatg

Cxcl1:
                                   (SEQ ID NO: 13)
F: tggctgggattcacctcaag;

                                   (SEQ ID NO: 14)
R: caagcctcgcgaccattct

Cxcl10:
                                   (SEQ ID NO: 15)
F: gccgtcattttctgcctcat;

                                   (SEQ ID NO: 16)
R: gcttccctatgcccctcatt
```

Human Taqman® Assays:

B2M Hs00984230_m1, Saa1 Hs00761940_s1, Saa2 Hs01667582_m1, IL6 Hs00985639_m1, IL8 Hs99999034_m1, Ccl20 Hs01011368_m1, Reg3 g Hs00417999_m1, iNos Hs01075529_m1, Cxcl10 Hs00171042_m1, Fut2 Hs00382834_m1, IL15 Hs01003716_m1, IL18 Hs01038788_m1, Ccl5 Hs00982282_m1

Results

SFB-host Cell Co-culturing System

SFB strain (Bolotin et al., 2014) isolated from monoassociated mice was deposited at CNCM (Collection Nationale de Cultures de Microorganismes, 25 rue du Docteur Roux, Paris) on Dec. 23, 2014, under the accession number CNCM 1-4932 (*Arthromitus muris* strain referred to as SFB-mouse-NL). SFB were cultured with eukaryotic cells grown in low but physiological oxygen conditions (He et al., 1999) in a rich tissue culture medium containing bacterial medium components and additional supplements. SFB from monoassociated mice were collected, filtered through a 100-μm mesh, separated from most other faecal matter using a Nycodenz column and passed through a 5-μm filter to obtain a pure culture of unicellular intracellular offspring (average 0.7 μm) (FIG. 1*a*). Eukaryotic cells grown on tissue culture wells or transwells were placed in a humidified anaerobic cabinet, challenged with intracellular offspring, and kept at either strict anaerobic conditions within a sealed box or left in the anaerobic cabinet where the oxygen concentration was maintained at low levels (0.5-1.4% O2). After 4 days, bacterial growth in the culture supernatant was quantified by quantitative PCR (qPCR) using SFB-specific 16S rDNA primers (FIG. 1*b*) and confirmed using scanning electron microscopy (SEM) (FIG. 1*c*). SFB growth was observed in all conditions for most cell lines assayed but growth was usually enhanced on transwells compared with tissue culture wells and growth was significantly better in the presence of oxygen, revealing SFB to be a relatively aerotolerant anaerobe. Both human (TC7/HeLa) and mouse (mICcl2/CMT93) cell lines supported growth but the TC7 was the most resilient cell line generally supporting SFB growth most robustly. On the basis of temporal analysis, the highest exponential growth phase occurred between days 1 and 3, with an average maximum doubling time of 5.0 h (FIG. 1*d*).

Growth Requirements for SFB

SFB growth had a striking dependence on host cell number, decreasing in number with decreasing cell density (FIG. 1*e*). In addition, negligible growth occurred in medium alone, medium supplemented with cell lysate, or when cells were fixed before SFB challenge (FIG. 1*f*), indicating that live host cells are required for SFB proliferation. SFB also required close contact for efficient growth as only little growth (0-6%) occurred when intracellular offspring were added to the bottom chamber of transwells or when bacteria were placed in transwells above TC7 cells in tissue culture wells (FIG. 1*f, g*). Yet, as host cell contact was not an absolute requirement, it suggests that host cells may release a soluble factor that promotes SFB growth. To address the requirement for medium supplementation, SFB were grown on TC7 cells in complete medium or medium missing individual additives. Brain-heart infusion, a yeast/peptone/casein amino-acid mixture, and particularly iron supplementation were critical for SFB growth (FIG. 1*h, i*).

In the 1970s, transmission electron microscopy studies of SFB present in the murine gut led to a proposed life cycle: attachment to epithelial cells via the holdfast at the intracellular offspring tip leads to filamentous growth and is followed by a complex developmental progression that starts at the distal tip and ultimately leads to intracellular offspring formation and release (FIG. 2A) (Chase et al., 1976; Ferguson et al., 1979). According to this model, when filaments grow beyond 50 μm in length, the large primary filament segments start to undergo a symmetrical division to form smaller secondary segments. These differentiate by dividing asymmetrically to form a mother/daughter cell. The daughter cell becomes engulfed and subsequently divides to form two intracellular offspring within the surrounding mother cell segment. Intracellular offspring are then released from the filament by breakdown of the filament septa and cell wall and reattach to the host.

Figure 2:
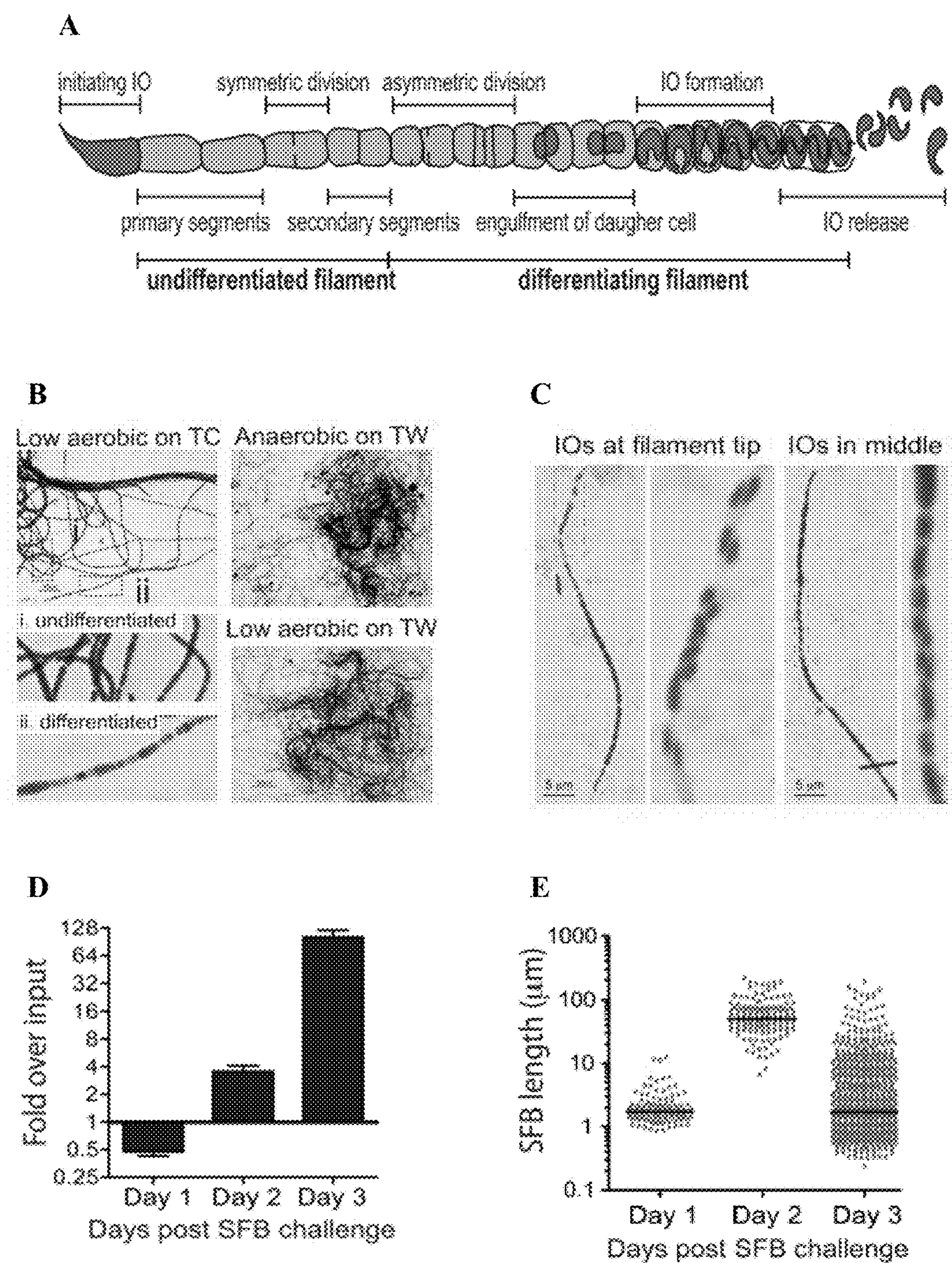
FIG. 2: Differentiation of SFB from filaments to intracellular offspring during in vitro growth. A, Schematic representation of an SFB filament highlighting stages of its growth and differentiation. Gram stain of SFB after 4 days of growth on B, TC7 cells incubated at the indicated condition, and C, TC7 cells grown on transwells in low oxygen. Analysis of SFB grown on mICcl2 cells (D-G) and TC7 cells (H) on transwells at 1-2.5% O2: D, qPCR quantification (mean±s.d. of triplicates); E, length of individual SFBs; F, Gram stain; and G, segment length analysis of representative 2-day-old SFB filaments. H, SEM of SFB after 4 days of growth. B-H, Representative images and values from one of three experiments performed in triplicate with (D) means±s.d.
Figure 2:
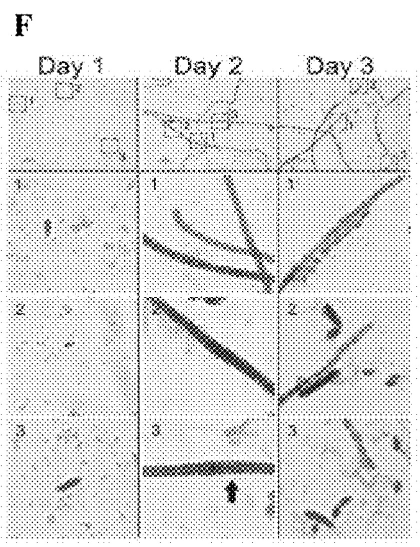
Figure 2:
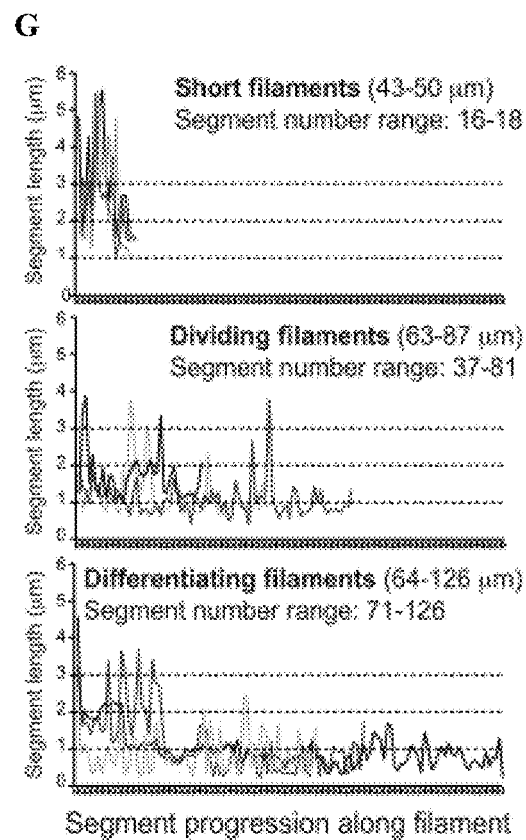
Figure 2:
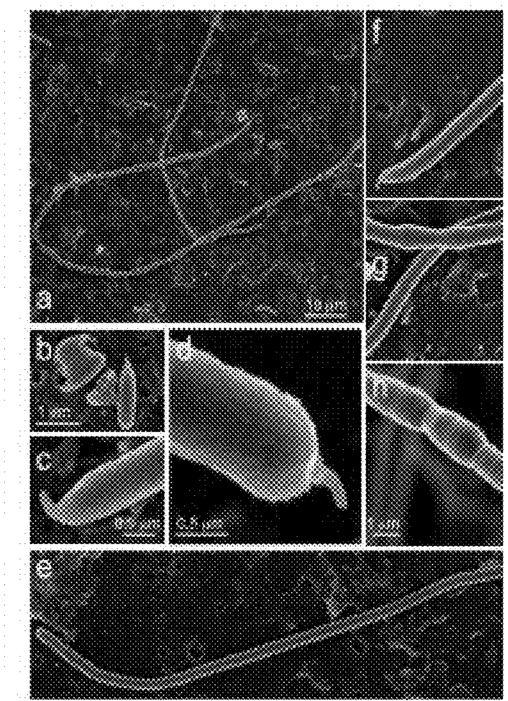

In vitro, growth of SFB on TC7 cells often yielded considerable quantities of long filaments that could be clumped together in a hairball-like phenotype easily seen with the naked eye (FIG. 2B). Most of these filaments were undifferentiated after 4 days, with only some filaments showing a characteristic heterogeneous staining of differentiating filaments (FIG. 2B, left-hand column, bottom two panels). Intracellular offspring could be seen located at the filament tip or occasionally in the central part of a filament (FIG. 2C), similar to filaments recovered from SFB-monoassociated mice (data not shown). Differentiation of SFB occurred on all four cell lines tested, but we noticed that differentiation was more pronounced when higher oxygen concentrations (1-2.5%) were used. In time-course analysis at this higher oxygen concentration (FIG. 2D), only short bacteria were detected 1 day after challenge (FIG. 2E, F). After 2 days, only long filaments were present (FIG. 2E, F) and the bacterial septa could be identified quite clearly using the Gram stain (FIG. 2F). Three types of filament were found (FIG. 2F, G): short filaments with long intracellular segments of ~2.6 μm; medium-sized filaments with smaller intracellular segments of ~1.2 μm; and medium to long filaments that had a more heterogeneous distribution of segment lengths including very small segments (FIG. 2F, G) and rare segments with half-circular structures (FIG. 2F, Day 2-3, arrow) that resembled the engulfment of a daughter cell by a mother cell. After 3 days of growth, most filaments had differentiated, at least in part, to the final intracellular offspring stage and intracellular offspring could be seen in a characteristic doublet orientation at the filament tip where the filament cell wall appeared to have lost its structure (FIG. 2F, far left column). Many intracellular offspring of varying lengths were also no longer associated with filaments. SEM confirmed the presence of the needle-like holdfast structure on intracellular offspring and at the tip of filaments (FIG. 2H, b-g), and could clearly distinguish between undifferentiated thin and smooth filaments (FIG. 2H, a, e-g) and those that were broader with a heterogeneous and bulbous morphology that corresponded to differentiating filaments (FIG. 2H, a, g, h) (Chase et al., 1976; Ferguson et al., 1979). In addition, cell-wall remnants could be detected at the distal tip of differentiating filaments where intracellular offspring had been released (FIG. 2H, h and Extended Data FIG. 1*b*) (Chase et al., 1976). Together, these data demonstrate that in vitro culturing of SFB supports the full differentiation of in vitro-grown SFB filaments to the intracellular offspring stage and confirms the SFB life cycle inferred from in vivo observations.

Viability and Infectivity of In Vitro Formed Intracellular Offspring

Figure 3:
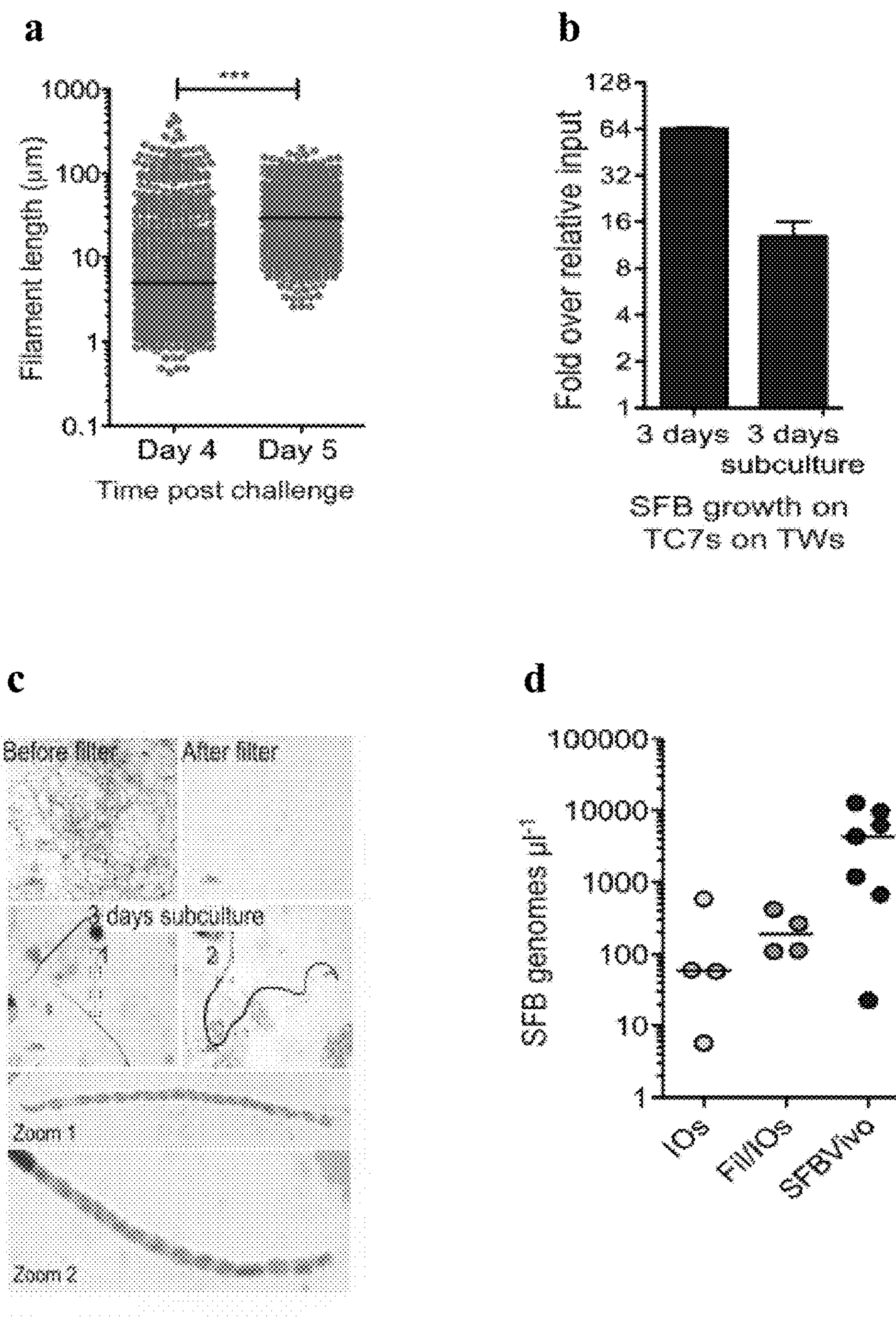
FIG. 3: Viability, colonization, and immunostimulatory potential of in vitro-grown SFB. a, SFB length after growth on TC7 cells on transwells; b, quantification and c, Gram stain of SFB growth on TC7 cells on transwells before and after a 3-day sub-culturing of the 5-μm filtrate; d-k, analysis of germ-free C57BL/6 mice gavaged with either filament/intracellular offspring mix, intracellular offspring, or faeces of SFB-monoassociated mice (SFB Vivo); d, quantification of ileum-associated SFB; e, k, Host gene expression in the ileal lamina propria; representative flow cytometry plots and quantification of (f, g) B220+ B cell and (i, j) CD45+CD3+CD4+ T cell frequencies of the indicated markers; h, faecal secretory IgA quantification by ELISA. a-k, Images and values are representatives from one of two experiments performed (a-c) in duplicate with means±s.d. or (d-k) performed with four to six mice per group. Statistical analysis using the two-tailed t-test (***P=<0.001).
Figure 3:
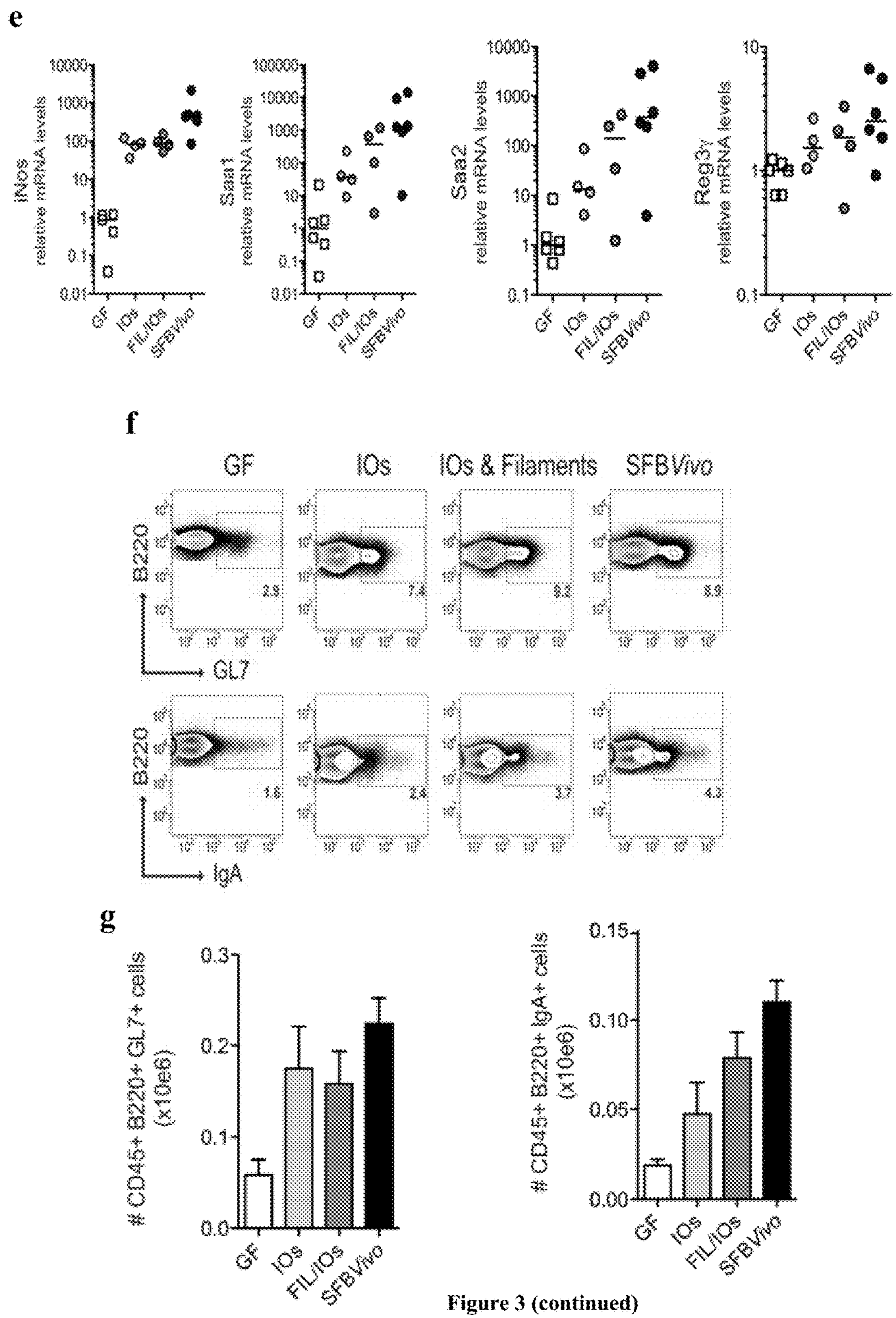
Figure 3:
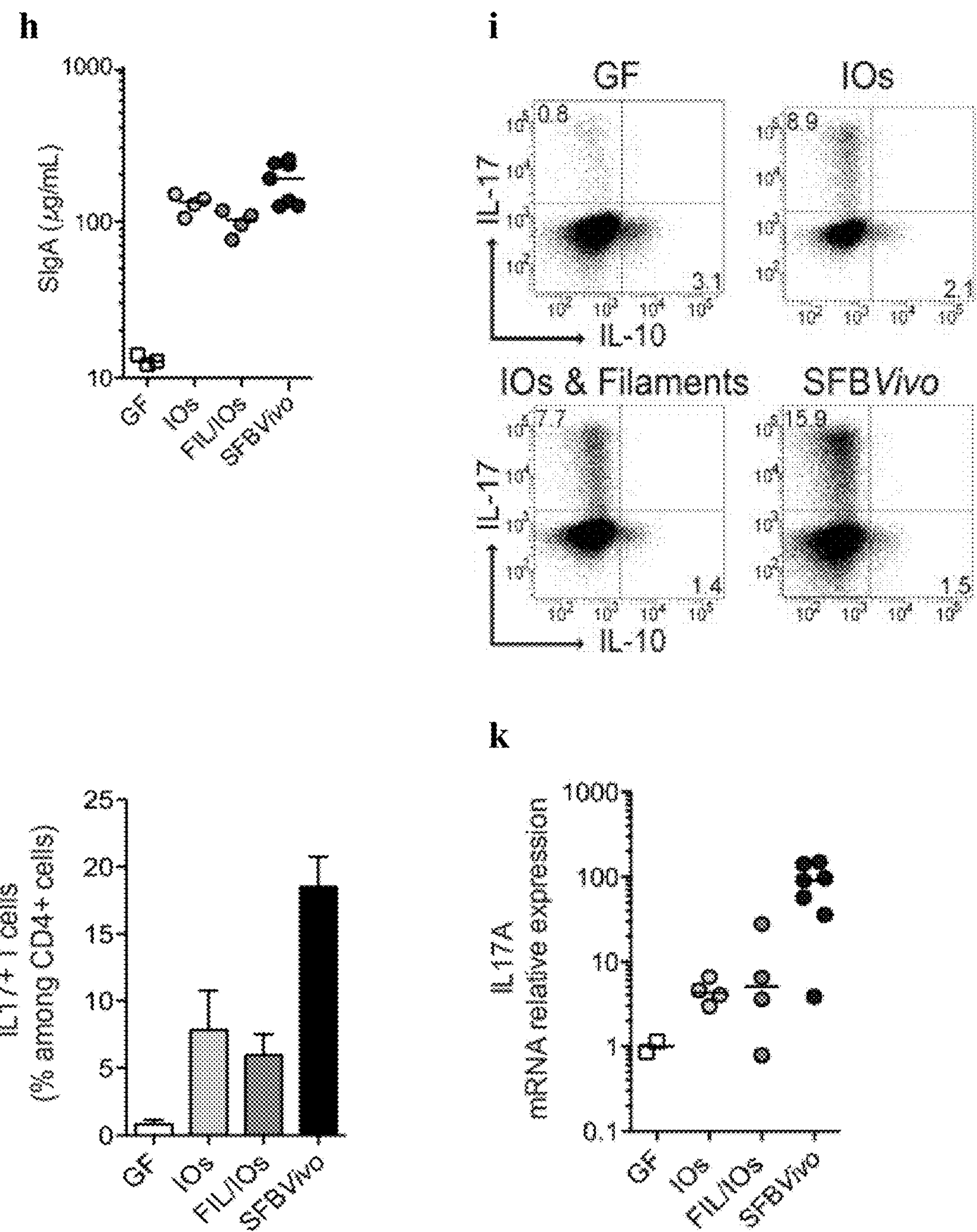
Figure 5:
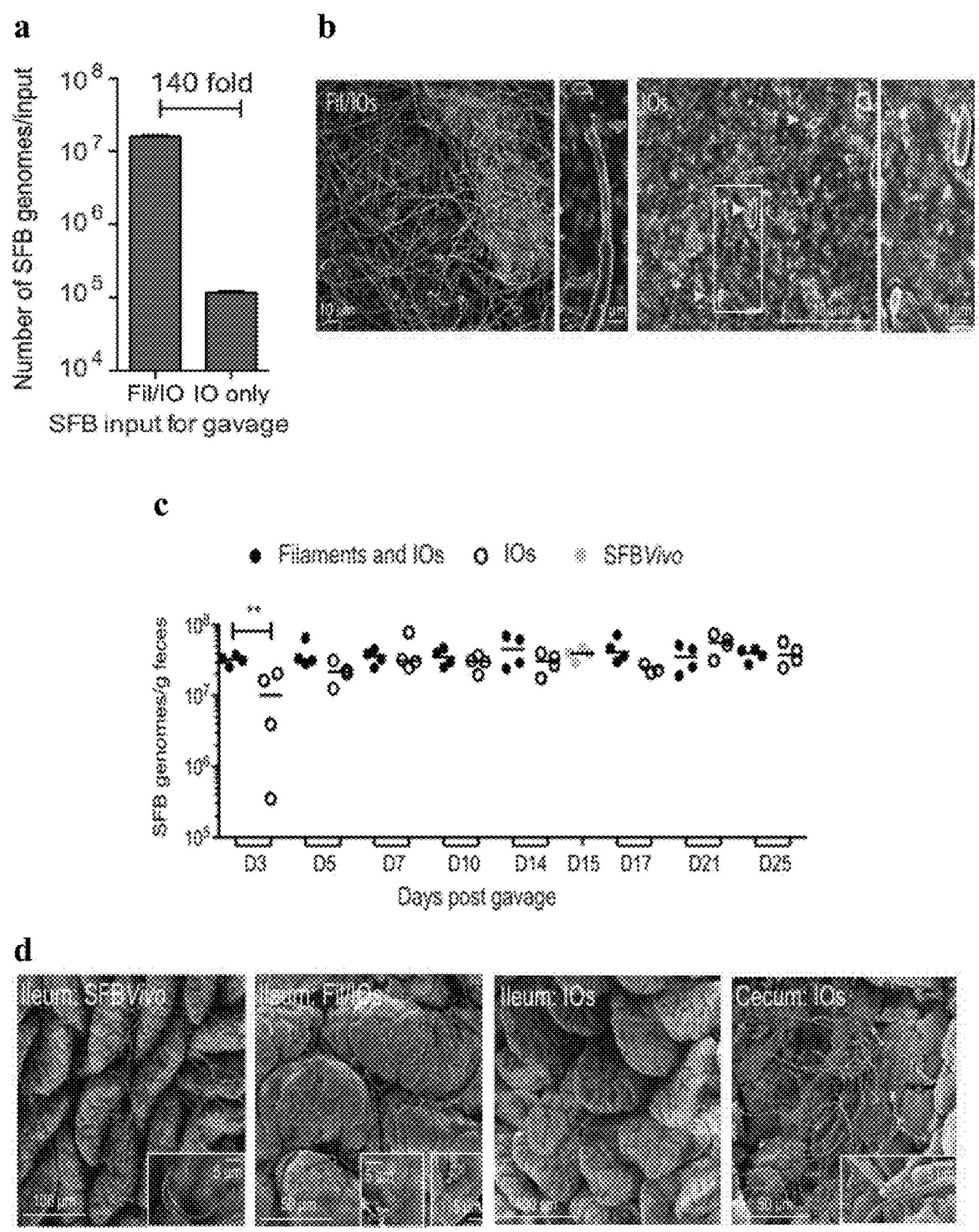
FIG. 5. Intestinal colonization of in vitro-grown SFB and host response. a, b, qPCR quantification (a) and SEM (b) of in vitro-grown SFB used for gavage. c, qPCR quantification of SFB in faecal samples. d, SEM of SFB attachment in vivo at 25 days after gavage of C57BL/6 mice with SFB Vivo or SFB Vitro. e, SEM of 21-day SFBcolonized germ-free C3H/HeN mouse ileum showing vacant attachment sites. f, Host gene expression in the ileal lamina propria in conventional or germ-free mice colonized with either SFB or *E. coli* for 21 days. Images and values are representatives from one of two experiments (a-e) or are cumulative values from two experiments performed with a total of seven germ free, four SFB, five *E. coli*, and four conventional mice (f), showing box plots of 25-75% centiles with median and minimum/maximum whiskers. c, f, Two-tailed t-test statistical analysis (*P=<0.05, **P=<0.01).
Figure 5:
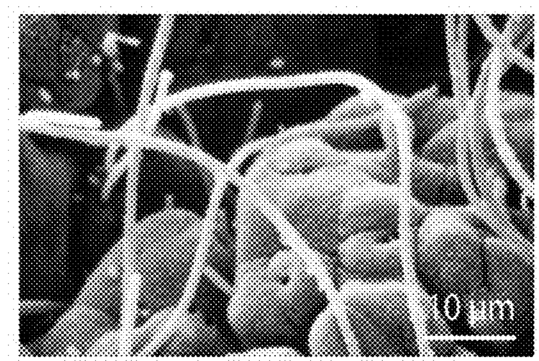
Figure 5:
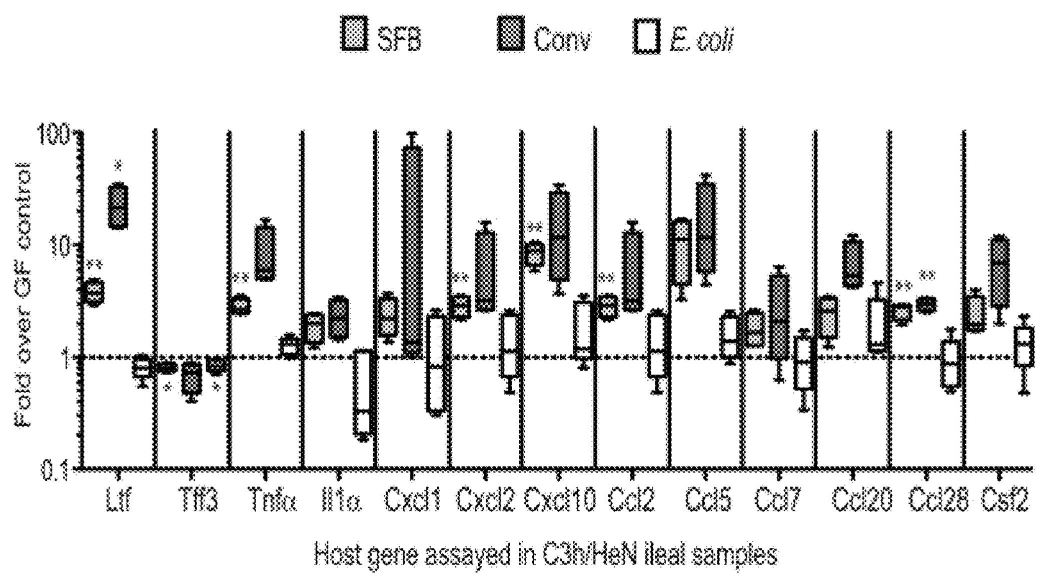

SFB were first grown on TC7 cells under aerobic conditions (FIG. 3*a*) until many intracellular offspring appeared. After one additional day, intracellular offspring were no longer present and the average bacterial length was significantly longer, indicating intracellular offspring outgrowth into filaments. Similarly, when intracellular offspring grown in vitro were separated from filaments by filtration through a 5-μm filter and added to newly plated cells, SFB numbers increased and the newly formed filaments differentiated into intracellular offspring at the filament tip (FIG. 3*b, c*), demonstrating filamentation and differentiation of in vitro-formed intracellular offspring. To assess whether SFB grown in vitro retained their ability to colonize mice and stimulate the characteristic innate and acquired immune responses, SFB grown in vitro for 3 days were divided into a filament/intracellular offspring fraction and a pure intracellular offspring fraction (FIG. 5*a, b*) and gavaged into germ-free mice. Colonization was firmly established by both inputs at 5 days after gavage (FIG. 5*c*) despite a 140-fold input difference for the filament/intracellular offspring and intracellular offspring fractions. However, unlike mice gavaged with SFB derived from faecal samples (SFB Vivo), which generally showed good colonization of the ileum, mice gavaged with in vitro-grown SFB (SFB Vitro) had much lower numbers of SFB colonizing the ileum (FIG. 3*d* and Extended Data FIG. 1*d*); instead they showed heavy colonization of the caecum (FIG. 5*d*). Thus, although SFB Vitro clearly can attach to the ileum, these results suggest that ileal colonization may be more efficient by intracellular offspring released from spores found in the faecal input, possibly because of the expression of flagella at this particular stage of the life cycle (Pamp et al., 2012). Notably, the magnitude of the innate host response (FIG. 3*e*) was proportional to the colonization level of the ileum (FIG. 3*e*) and not the overall SFB faecal load (Extended Data FIG. 1*c*), revealing the requirement for ileal attachment of SFB to induce the innate host response. Similar to SFBVivo, albeit with less potency, SFB Vitro were also able to stimulate the B-cell compartment in Peyer's patches (FIG. 3*f, g*), enhance IgA secretion in the faeces (FIG. 3*h*), and increase the number of Th17 cells and the level of IL-17A messenger RNA in the small intestine lamina propria (FIG. 3*i-k*).

SFB-host Interaction and the Host Response to SFB Growth.

Figure 4:
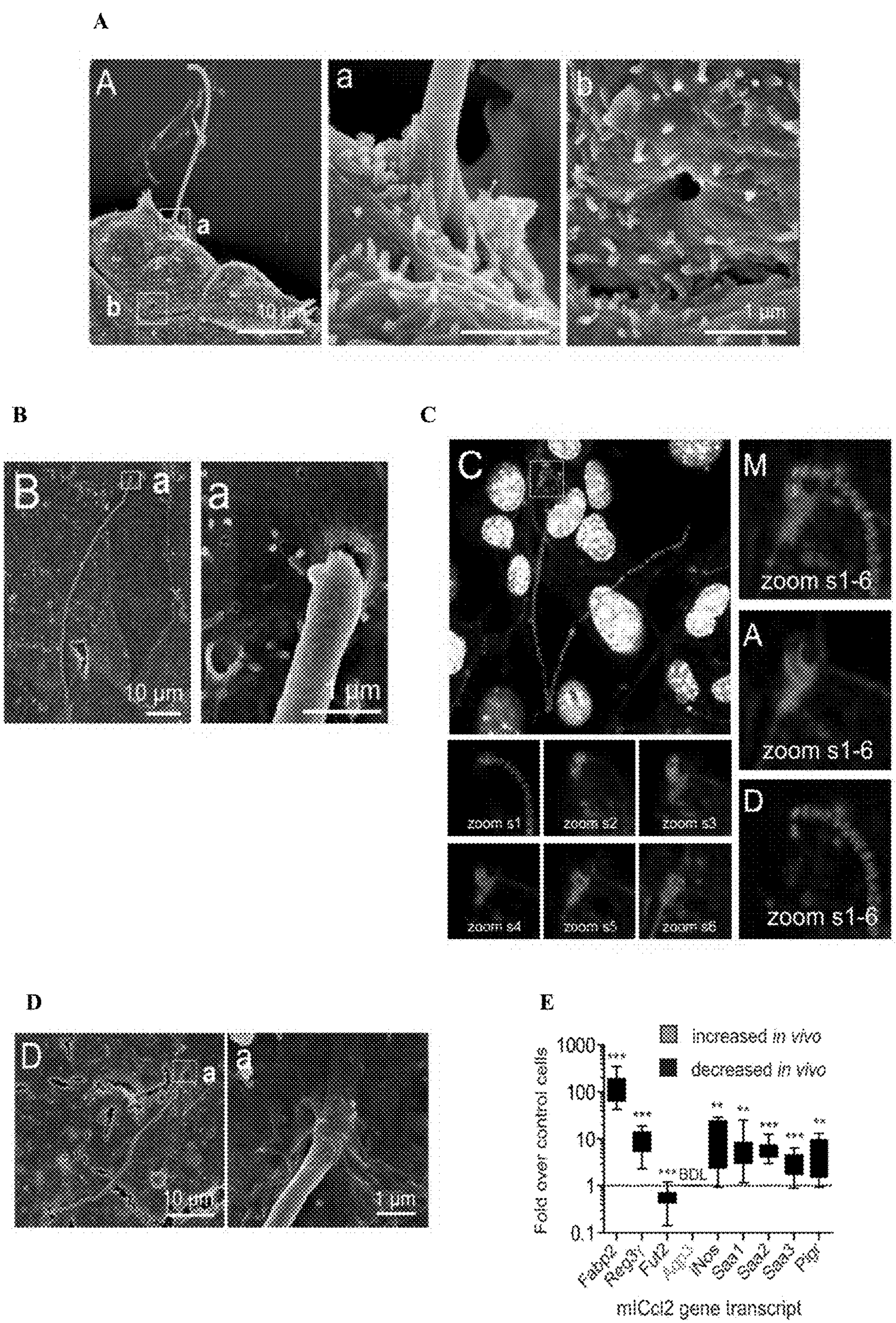
FIG. 4: SFB-host cell interaction and host response. SEM of SFB attached to subconfluent (A) and confluent (B) mICcl2 cells after 2 days of intracellular offspring challenge. C, Merge (M) of 4',6-diamidino-2-phenylindole (DAPI) (D) and actin (A) stain of mICcl2 cells challenged with intracellular offspring for 2 days showing confocal slices (s) and Z-projections. D, SEM of 3-day-old SFB filament attached to TC7 cells. Host response using qPCR analysis of mICcl2 cells (E, F, H) and TC7 cells (G) 3 days after challenge with (E-G) SFB or (H) various MAMPs. NS, not significant; BDL, below detection limit. Images and values are representatives from one of two experiments performed in triplicate (A-D) or are cumulative values from four experiments performed in triplicate with box plots of 25-75% centiles with min/max whiskers (E-G) or means±s.e.m.; (H) with a two-tailed t-test statistical analysis (*P=<0.05, P=<0.01, *P=<0.001).
Figure 4:
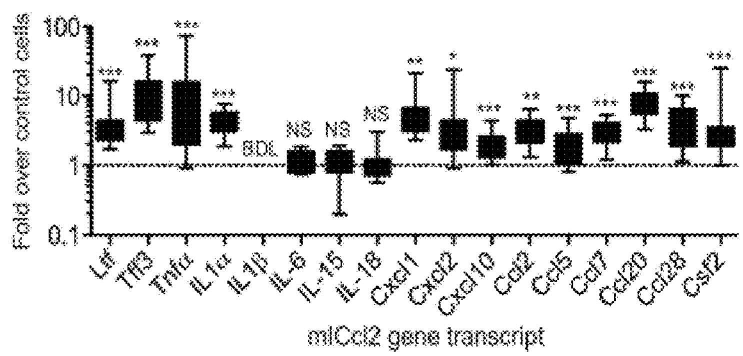
Figure 4:
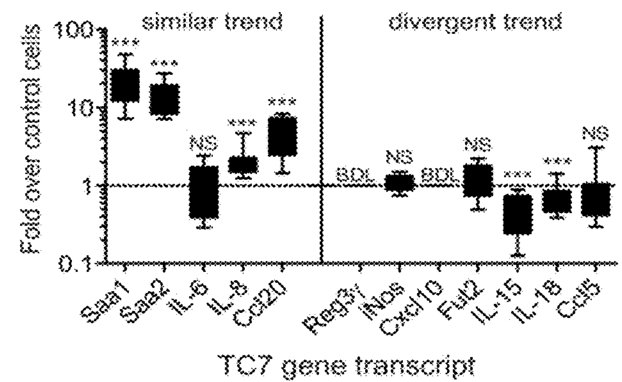
Figure 4:
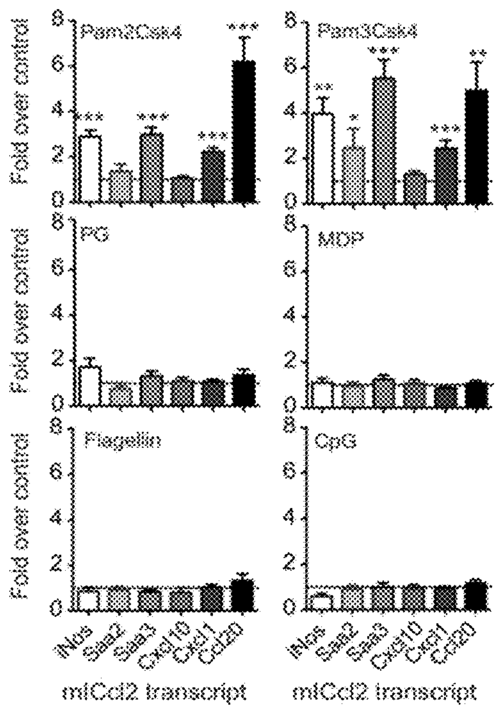

Despite the apparent requirement for close contact between host cells and SFB for efficient growth, a tight interaction was not readily observed. However, when the interaction was promoted by gently spinning intracellular offspring onto cells, SFB filaments were found attached to mICcl2 cells (FIG. 4A-C). This stable interaction was accompanied by actin accumulation surrounding the filament tip (FIG. 4C) and could leave structurally intact vacant W attachment sites (FIG. 4A, c), similar to those observed in the ileum of mice (FIG. 5*e*). Attached filaments included both undifferentiated ones and those that had reached the final intracellular offspring stage. Contrary to in vivo results (Tannock et al., 1984), attachment in vitro was not species specific (FIG. 4D). To assess the similarity in the host response to SFB in vitro and in vivo, it was analysed the gene expression profile of epithelial derived host factors known to be regulated by SFB colonization (Ivanov et al., 2009; Gaboriau-Routhiau et al., 2009; Goto et al., 2014; Shima et al., 2008; Lécuyer et al., 2014). It was found that the gene regulation in vitro closely recapitulated gene regulation in vivo (FIG. 4E), thereby further supporting the in vitro model system. Going beyond previously implicated epithelial factors, it was tested several additional cytokines, chemokines, and host defence genes (FIG. 4F). The data show that SFB growth leads to a strong inflammatory host response, with the induction of pleiotropic inflammatory mediators such as tumour-necrosis factor-α (TNF-α), interleukin-1-α (IL1-α), and serum amyloid A 1-3 (Saa1-3), induction of several innate host defence mechanisms (Reg3γ, iNos, and lactoferrin), and an immunological environment that is conducive for the recruitment of B cells, the transmigration of IgA, recruitment and activation of T cells, and recruitment of neutrophils, dendritic cells, as well as monocytes. In agreement, it was observed that the transcript level of most immune genes that are upregulated during co-culture with mICcl2 cells in vitro was also increased by SFB, and not by *Escherichia coli*, during colonization experiments in vivo (FIG. 5*f*). Conversely, the transcriptional response in the human TC7 cell line was divergent from that observed in mICcl2 cells and less consistent with in vivo results (FIG. 4*g*). Lastly, by using an array of microbe-associated molecular patterns (MAMPs), it was demonstrated that the inflammatory response to SFB in vitro is probably shaped by the activation of TLR2 (FIG. 4*h*).

Conclusion

These data demonstrate the successful culturing of SFB in vitro and provide new insights into SFB growth requirements and the host response to SFB challenge. These data suggest that in vivo, attachment of SFB to the ileal surface is an important feature to elicit epithelial cell responses, whereas in vitro, where attachment remained infrequent, the close proximity of SFB and cells appears largely to bypass the need for attachment to deliver the stimulating signal(s). These findings highlight the importance of the privileged location of the replicative niche of SFB at the ileal epithelial surface in mediating the stimulatory potential of SFB.

EXAMPLE 2

Methods for Genetically Modifying a SFB Strain

A series of modular shuttle vectors designed for use in Clostridia species (Heap et al., 2009) are tested for their ability to be stably introduced into SFB during in vitro growth using both conjugation and transformation. Each plasmid contains a different origin of replication with a choice of antibiotic resistance cassettes, multiple cloning sites and promoters. Conjugation and transformation are performed during in vitro growth of SFB.

Conjugation

An auxotrophic *E. coli* strain requiring the addition of Diaminopimelic acid to the medium for growth is used as a donor strain as this strain can be easily selected against in rich medium with the absence of diaminopimelic acid.

SFB strain is purified from monoassociated mice as described above and intracellular offsprings (IOs) are added to host cells (TC7 cells) grown on either tissue culture or transwell plates under conditions described for SFB growth above.

After substantial growth has occurred (2-4 days), diaminopimelic acid (100 ug/ml) and the donor *E. coli* strain (requiring dap addition for growth and carrying a plasmid) is added and centrifuged together with cells and SFB and maintained for a given time (e.g., 4-8 hours).

Alternatively, in vitro grown (cultured) SFB are collected and mixed with the aforementioned *E. coli* strain and pelleted (all under low oxygen) and maintained in a pellet for varying amounts of time (e.g., 4-8 hours).

Bacteria are collected and washed 2× with regular SFB growth medium lacking diaminopimelic acid before being put on fresh eukaryotic cells (always at low oxygen) with regular SFB medium but complemented with the appropriate antibiotic to which the conjugal plasmid gives SFB resistance to.

After a given time (0-24 hours), SFV are collected and gavaged into germfree mice.

Recombinant SFB are selected for and maintained by antibiotic treatment of the drinking water. The optimal and minimal regime of antibiotic use in the drinking water that is needed to cure SFB monoassociated mice from SFB is determined prior and used to select for recombinant SFB.

Transformation by Electroporation

As described above, SFB are grown (cultured) in vitro for 2-4 days on TC7 cells.

SFB are collected and put on ice. Under low oxygen conditions and working with solutions put on ice, SFB are washed 6× with 10% glycerol/pre-equilibrated water before being resuspended and concentrated with 10% glycerol/H2O.

Purified plasmid DNA is added and SFB is electroporated (6.5 $kV\cdot cm^{-1}$ to 25 $kV\cdot cm^{-1}$).

SFB are placed in regular SFB medium again and spun onto fresh cells. SFB are allowed to recover for 3-24 hours before selective antibiotic be added overnight.

SFB are gavaged into GF mice.

Recombinant SFB are selected for and maintained by antibiotic treatment of the drinking water.

Transformation by the Chemical Method: Calcium Chloride and Heat Shock

As described above, SFB are grown in vitro for 2-4 days on TC7 cells.

SFB are collected and put on ice. Under low oxygen conditions and working with solutions put on ice, SFB are washed 5× with 0.1M calcium chloride before being resuspended and concentrated with 10% glycerol/0.1M calcium chloride.

Purified plasmid DNA is added to SFB and incubated for 30 minutes.

SFB are heat shocked at 42° C. for 30 seconds before being placed in regular SFB medium again and spun onto fresh cells. SFB are allowed to recover for 3-24 hours before selective antibiotic be added overnight.

SFB are gavaged into GF mice.

Alternatively, the above procedure may be performed at room temperature only without heat shock.

Recombinant SFB are selected for and maintained by antibiotic treatment of the drinking water.

REFERENCES

Bolotin, A. et a, *Genome Announc.* 2, 1-2 (2014).
Chappert, P. et al., *Immunity* 38, 1198-1210 (2013).
Chase, D. G. & Erlandsen, S. L., *J Bacteria* 127, 572-583 (1976).
Danchin A., *Molec. gen. Genet.* 150, 293-299 (1977).
Davis, C. P. and Savage, D. C., *Infection and Immunity* 13, 180-188 (1976).
Ericsson, A. C., et al., Comparative Medicine, 64, 90-98 (2014).
Ferguson, D. J. & Birch-Andersen, A., *Acta Pathol. Microbiol. Scand. B* 87, 247-252 (1979).
Ferreira, P. C. D. et al., *FEMS Immunol Med Microbiol.* 54, 245-254 (2008).
Ferreira, P. C. D. et al., *Clinical and Vaccine Immunology* 18, 1823-1833 (2011).
Fleckenstein, J. et al., *Expert Review of Vaccines* 13, 631-639 (2014).
Gaboriau-Routhiau, V. et al. *Immunity* 31, 677-689 (2009).
Ghaem-Maghami, M. et al., *Infect. Immun.* 69, 5597-5605 (2001).
Godon, J. J. et al., *Appl. Environ. Microbiol.* 63, 2802-2813 (1997).
Goto, Y. et al., *Science* 345, 1254009 (2014).
He, G. et al., *Proc. Natl Acad. Sci. USA* 96, 4586-4591 (1999).
Heap, J. T., et al., *J. Microbiol. Methods,* 78, 79-85 (2009).
Heine, S. J. et al., *Vaccine* 31, 2919-2929 (2013).
Ivanov, I. I. et al., *Cell* 139, 485-498 (2009).
Jepson, M. A. et al., *Infect. Immun.* 61, 4001-4004 (1993).

Kaper, J. B. et al., *Nat Rev Micro* 2, 123-140 (2004).
Klaasen, H. et al., *FEMS Microbiol.* 88, 165-180 (1992).
Kriegel, M. A. et al., *Proc. Natl Acad. Sci. USA* 108, 11548-11553 (2011).
Kuwahara, T. et al., *DNA Res.* 18, 291-303 (2011).
Lécuyer, E. et al., *Immunity* 40, 608-620 (2014).
Lee, Y. K. *Proc. Natl Acad. Sci. USA* 108 (Suppl 1), 4615-4622 (2011).
Martinez-Becerra, F. J. et al., *Infect. Immun.* 80, 1222-1231 (2012).
Mills, J. A. et al., *Infect. Immun.* 56, 2933-2941 (1988).
Paccez J. D. et al., *Vaccine* 25, 4671-4680 (2007).
Pamp, S. J. et al., *Genome Res.* 22, 1107-1119 (2012).
Parsot, C. *Curr. Opin. Microbiol.* 12, 110-116 (2009).
Prakash, T. et al., *Cell Host Microbe* 10, 273-284 (2011).
Schnupf, P. & Sansonetti, P. J., *PLoS ONE* 7, e36446 (2012).
Schnupf, P. et al., *Semin. Immunol.* 25, 342-351 (2013).
Sczesnak, A. et al., *Cell Host Microbe* 10, 260-272 (2011).
Shima, T. et al., *FEMS Immunol. Med. Microbiol.* 52, 69-77 (2008).
Tannock, G. W. et al., *Appl. Environ. Microbiol.* 47, 441-442 (1984).
Wu, H. J. et al., *Immunity* 32, 815-827 (2010).
Yang, Y. et al., *Nature* 510, 152-156 (2014).
Yin, Y. et al. *ISME J.* 7, 615-621 (2012).
Yurkovetskiy, L. et al., *Immunity* 39, 400-412 (2013).

The invention claimed is:

1. An in vitro method of culturing a segmented filamentous bacterium (SFB) strain, comprising co-culturing said SFB strain with a eukaryotic host cell, wherein the culture is performed at an $O_2$ level of less than 5% in a rich tissue culture liquid medium comprising bacterial medium components and iron, and wherein the co-culture is performed until the SFB strain releases intracellular offspring or spores.

2. The method according to claim 1, wherein the SFB strain is a wild-type strain or a genetically modified strain.

3. The method according to claim 2, wherein the genetically modified SFB strain expresses an antigen of a diarrheal pathogen selected from the group consisting of *Shigella*, enterotoxic *Escherichia coli*, and attaching and effacing lesion (A/E)-inducing enteropathogenic *Escherichia coli*.

4. The method according to claim 3, wherein the antigen is *Shigella* IpaB protein or IpaD protein.

5. The method according to claim 3, wherein the antigen is an enterotoxic *Escherichia coli* antigen selected from colonization factor antigen I, adhesin CfaE, a heat-labile toxin, and nontoxic B subunit of heat-labile toxin.

6. The method according to claim 3, wherein the antigen is an attaching and effacing lesion (A/E)-inducing enteropathogenic *Escherichia coli* intimin, or a fragment encoding amino adds 363 to 808 of the 94 kDa beta-intimin antigen.

7. The method according to claim 2, wherein the SFB strain is isolated from a mammal.

8. The method according to claim 7, wherein the SFB strain is isolated from a mammal selected from the group consisting of a human and a mouse.

9. An in vitro method of culturing a SFB strain, comprising the steps of:

a) growing eukaryotic host cells on a solid culture medium;

b) transferring the eukaryotic host cells grown in step a) into a eukaryotic host cell-SFB liquid culture medium to provide a cell culture;

c) challenging the cell culture of step b) with a SFB strain; and d) co-culturing the eukaryotic host cells and the SFB strain in the liquid culture medium at an $O_2$ level of less than 5%, wherein the co-culture is performed until the SFB strain releases intracellular offspring or spores.

10. The method according to claim 9, wherein the eukaryotic host cell is an epithelial cell or a cancer cell.

11. The method according to claim 9, wherein the eukaryotic host cells are gastrointestinal tract cells or carcinoma cells.

12. The method according to claim 9, wherein the eukaryotic host cells are selected from the group consisting of human Caco-2 cell line cells, human TC7 cell line cells, human HeLa cell line cells, mouse mICcl2 cell line cells, and mouse CMT93 cell line cells.

13. The method according to claim 9, wherein in step a) the eukaryotic host cells are grown at an $O_2$ level of from 0% to 5%.

14. The method according to claim 9, wherein in step a) the eukaryotic host cells are grown at an $O_2$ level of from 0.5 to 3%.

15. The method according to claim 9, wherein in step a) the eukaryotic host cells are grown at an $O_2$ level of from 1 to 2.5%.

16. The method according to claim 9, wherein in step b) the eukaryotic host cell-SFB liquid culture medium is a rich tissue culture medium comprising bacterial medium components and iron.

17. The method according to claim 16, wherein the liquid culture medium comprises brain-heart infusion and a yeast/peptone/casein amino-acid mixture.

18. The method according to claim 16, wherein the liquid culture medium is supplemented with from 1% to 5% decomplemented fetal calf serum.

19. The method according to claim 16, wherein the liquid culture medium is supplemented with from 1% to 3% decomplemented fetal calf serum.

20. The method according to claim 16, wherein the liquid culture medium is supplemented with 2% decomplemented fetal calf serum.

21. The method according to claim 16, wherein the liquid culture medium further comprises sugars, retinoic acid and/or nucleotides.

22. The method according to claim 16, wherein the iron is in the form of $Fe^{2+}/Fe^{3+}$, $3{\times}Fe^{2+}$, $3{\times}Fe^{2+}$ or hemin.

23. The method according to claim 16, wherein the iron concentration is from 0.015 to 0.05 mM.

24. The method according to claim 16, wherein the iron concentration is from 0.02 to 0.04 mM.

25. The method according to claim 9, wherein the liquid culture medium comprises DMEM/F12 advanced medium, supplemented with fetal calf serum, non-essential amino acids, 4-(2-hydroxyethyl)-1-piperazineethanesulfonic acid, brain-heart infusion, a yeast/peptone/casein amino-acid mixture and iron.

26. The method according to claim 9, wherein in step c) the SFB strain is in the form of a filament or an intracellular offspring.

27. The method according to claim 9, wherein in step c), the SFB strain is directly contacted with the eukaryotic host cells.

28. The method according to claim 27, wherein the co-culture of the eukaryotic host cells and the SFB strain is performed at an $O_2$ level of from 0.5 to 3%.

29. The method according to claim 9, wherein the co-culture of the eukaryotic host cells and the SFB strain is performed at an $O_2$ level of from 0% to 5%.

30. The method according to claim 9, wherein the co-culture of the eukaryotic host cell and the SFB is performed at an $O_2$ level of from 1 to 2.5%.

31. The method according to claim 9, wherein iron is at a concentration of from 0.015 to 0.05 mM.

32. The method according to claim 9, further comprising recovering the cultured SFB strain, wherein the cultured SFB strain is recovered in a form of at least one of a filament, an intracellular offspring and a spore.

33. The method according to claim 9, wherein the SFB strain is a wild-type strain or a genetically modified strain.

34. The method of claim 9, wherein the eukaryotic host cells grown in step a) are grown until a cell confluence of at least 20% is obtained.

35. The method of claim 9, wherein the eukaryotic host cells grown in step a) are grown until a cell monolayer is obtained.

36. The method of claim 9, wherein the eukaryotic host cells grown in step a) are plated on a plate.

37. The method of claim 9, wherein the eukaryotic host cells grown in step a) are plated on a tissue culture well or transwell, prior to step b).

38. The method of claim 9, wherein the seeding density of the eukaryotic host cells in a) is between $1{\times}10^4$ and $6{\times}10^4$ cells per $cm^2$.

39. The method according to claim 9, wherein the SFB strain is added in step c) when the culture density of the eukaryotic host cells is from $0.5{+}10^5$ to $3{\times}10^5$ cells per $cm^2$.

40. The method according to claim 9, wherein the ratio in step c) between the eukaryotic host cells and the SFB strain is from 0.1 to 100.

41. The method according to claim 40, wherein the ratio between the eukaryotic host cells and the SFB strain is from 0.3 to 60.

42. The method according to claim 9, wherein the co-culture is performed for a duration selected from the group consisting of 1, 2, 3, 4, 5 and 6 days.

43. The method according to claim 9, wherein d) comprises applying conditions to induce spore formation, selected from adding an oxidative stress and short-term culture in the presence of an antibiotic.

44. A food product comprising the recovered SFB strain made by the method of claim 32.

45. The food product according to claim 44, wherein the SFB strain is alive.

* * * * *